United States Patent [19]

Matiskella et al.

[11] Patent Number: 6,093,712

[45] Date of Patent: Jul. 25, 2000

[54] CEPHALOSPORIN DERIVATIVES

[75] Inventors: John D. Matiskella, Wallingford; Stanley V. D'Andrea, Middletown; Thomas W. Hudyma, Durham; Yasutsugu Ueda, Clinton; Oak K. Kim, Guilford; Raymond F. Miller, Killingworth; Shelley E. Hoeft, Groton; Joanne J. Bronson, Madison, all of Conn.

[73] Assignee: Bristol-Meyers Squibb Company, Princeton, N.J.

[21] Appl. No.: 09/209,122

[22] Filed: Dec. 10, 1998

Related U.S. Application Data

[63] Continuation-in-part of application No. 08/829,126, Mar. 28, 1997, abandoned
[60] Provisional application No. 60/031,974, Nov. 27, 1996, provisional application No. 60/020,660, Jun. 19, 1996, and provisional application No. 60/014,851, Apr. 4, 1996.

[51] Int. Cl.[7] ........................ C07D 501/36; A61K 31/546
[52] U.S. Cl. .......................... 514/203; 540/224; 540/225
[58] Field of Search ............................ 514/203; 540/224, 540/225

[56] References Cited

U.S. PATENT DOCUMENTS

| | | | |
|---|---|---|---|
| 5,620,969 | 4/1997 | Bronson et al. | 514/203 |
| 5,734,047 | 3/1998 | Kim | 540/224 |

FOREIGN PATENT DOCUMENTS

| | | |
|---|---|---|
| 209751 | 1/1987 | European Pat. Off. . |

OTHER PUBLICATIONS

Theodora W. Greene, "Protection for the Carboxyl Group," Protective Groups In Organic Synthesis, Chapter 5, pp. 152–192, John Wiley & Sons, 1981.

I.E. El–Kholy, et al, "Action of Amines and Carbonyl Reagents on 3,5–Diphenyl–4–Pyrone and Its Thio Analogue," J. Heterocyclic Chem., 11, pp. 487–490, 1974.

*Primary Examiner*—Mark L. Berch
*Attorney, Agent, or Firm*—David N. Morse

[57] ABSTRACT

Provided are cephem derivatives represented by the general formula

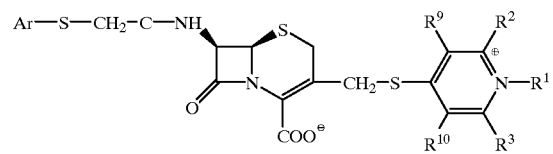

wherein Ar, $R^1$, $R^2$, $R^3$, $R^9$ and $R^{10}$ are as defined in the application. The derivatives are gram-positive antibacterial agents especially useful in the treatment of diseases caused by methicillin-resistant *Staphylococcus aureus*.

9 Claims, No Drawings

CEPHALOSPORIN DERIVATIVES

CROSS-REFERENCE TO RELATED APPLICATIONS

This application is a Continuation-in-Part of co-pending application U.S. Ser. No. 08/829,126 filed Mar. 28, 1997 abandoned, which application claims the benefit of U.S. Provisional Application Ser. No. 60/031,974 filed Nov. 27, 1996, U.S. Provisional Application Ser. No. 60/020,660 filed Jun. 27, 1996, and U.S. Provisional Application Ser. No. 60/014,851 filed Apr. 4, 1996.

BACKGROUND OF THE INVENTION

1. Field of the Invention

The present invention is directed to new cephem derivatives represented by the general formula

I

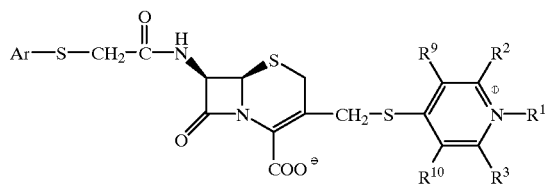

wherein Ar is a group of the formula

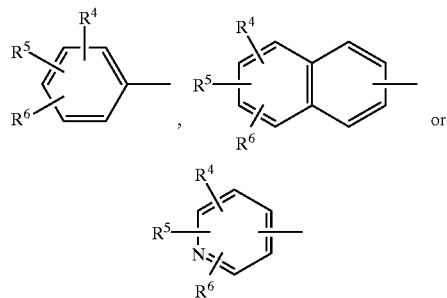

in which $R^4$, $R^5$ and $R^6$ are each independently hydrogen, halogen, trihalomethyl, nitro, amino, hydroxy, hydroxy $(C_1-C_6)$alkyl, $(C_1-C_6)$alkyl, $-(CH_2)_nOR^7$ or $-(CH_2)_nSR^7$; n is an integer of from 1 to 6; $R^7$ is hydrogen or $(C_1-C_6)$alkyl;

$R^1$ is

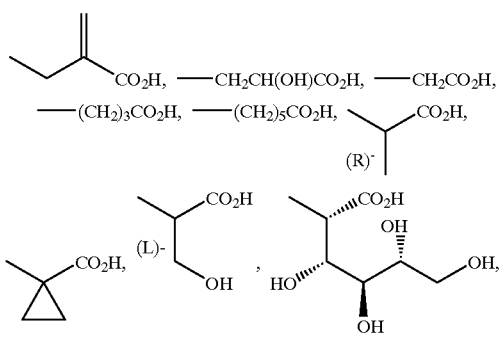

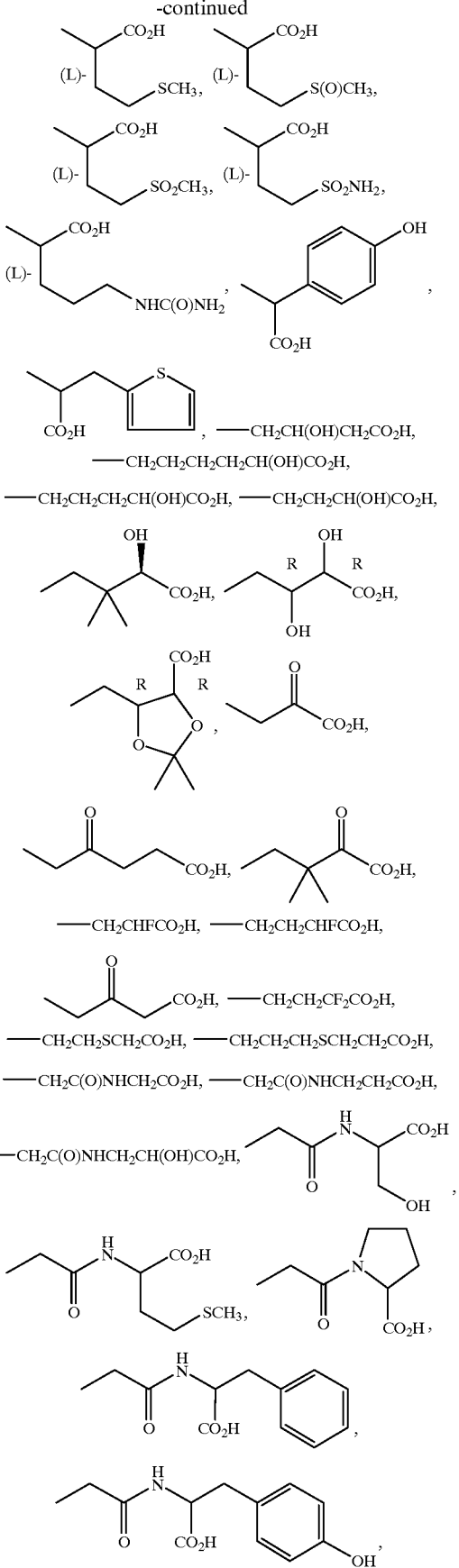

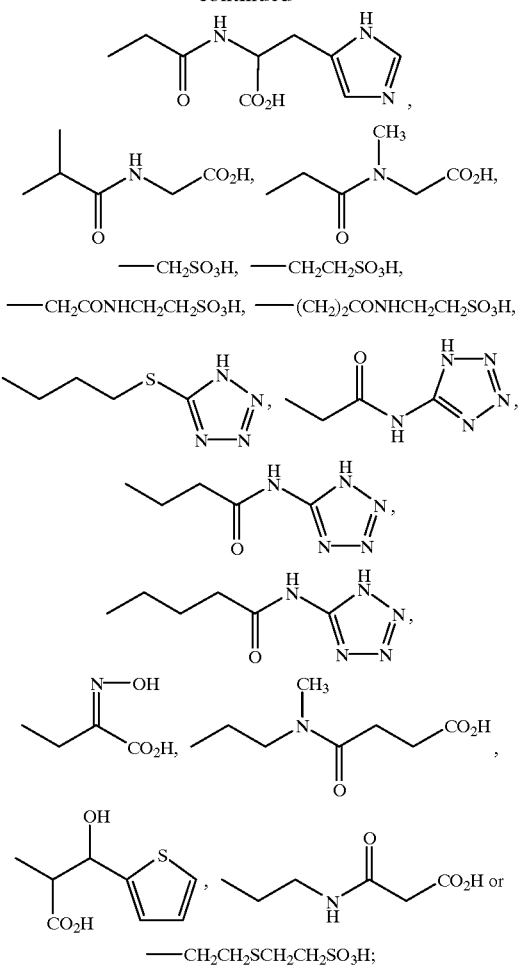

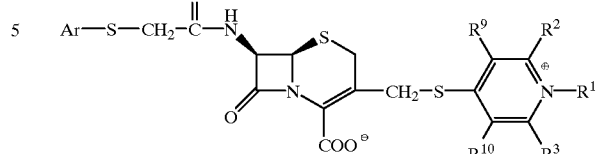

$R^2$, $R^3$, $R^9$ and $R^{10}$ are each independently hydrogen or $(C_1-C_{10})$alkyl; and pharmaceutically acceptable salts thereof. The derivatives are gram-positive antibacterial agents especially useful in the treatment of diseases caused by methicillin-resistant *Staphylococcus aureus* (also referred to below as MRSA or methicillin-resistant *S. aureus*).

2. Description of the Prior Art

The literature discloses a vast number of cephem derivatives having a wide variety of C-3 and C-7 substituents. Applicants are not aware, however, of any literature disclosing compounds with the combination of C-3 and C-7 substituents found by applicants to give the desired activity, solubility and toxicity profile needed for a commercially viable anti-MRSA cephalosporin product.

SUMMARY OF THE INVENTION

The present invention provides a novel series of cephem derivatives of the general formula

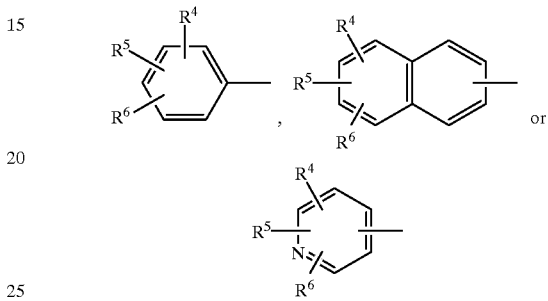

wherein Ar is a group of the formula in which $R^4$, $R^5$ and $R^6$ are each independently hydrogen, halogen, trihalomethyl, nitro, amino, hydroxy, hydroxy $(C_1-C_6)$alkyl, $(C_1-C_6)$alkyl, $-(CH_2)_nOR^7$ or $-(CH_2)_nSR^7$; n is an integer of from 1 to 6; $R^7$ is hydrogen or $(C_1-C_6)$alkyl;

$R^1$ is

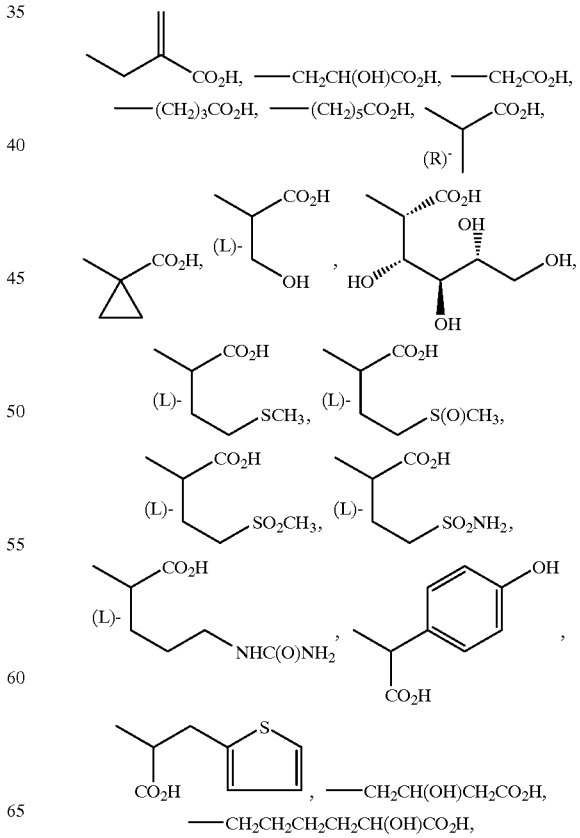

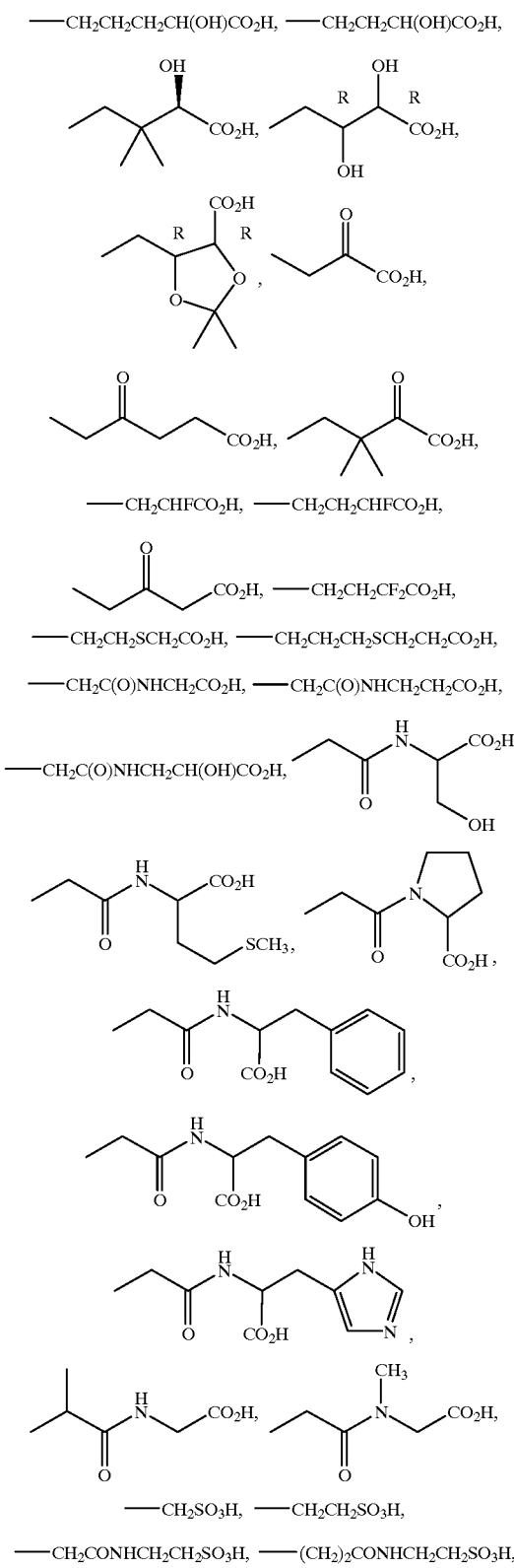

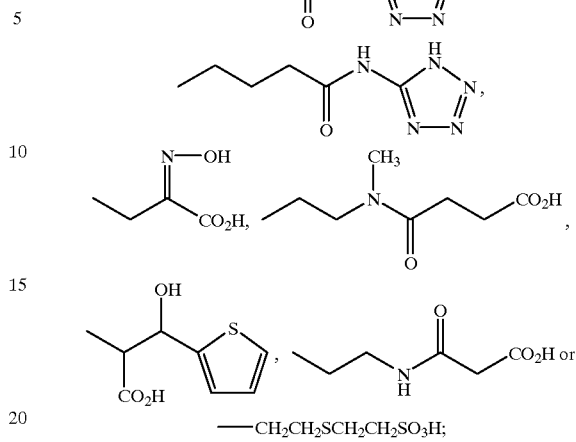

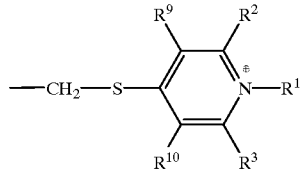

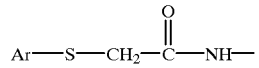

$R^2$, $R^3$, $R^9$ and $R^{10}$ are each independently hydrogen or $(C_1-C_{10})$alkyl; and pharmaceutically acceptable salts thereof.

The compounds of formula I are antibacterial agents useful in the treatment of infections in humans and other animals caused by a variety of gram-positive bacteria, particularly methicillin-resistant S. aureus.

Also included in the invention are processes for preparing the compounds of formula I and pharmaceutical compositions containing said compounds in combination with pharmaceutically acceptable carriers or diluents.

DETAILED DESCRIPTION

The present invention provides novel cephem derivatives of general formula I above which are antibacterial agents useful in the treatment of infectious diseases in humans and other animals. The compounds exhibit good activity against a variety of gram-positive microorganisms, e.g. S. pneumoniae, S. pyogenes, S. aureus. E. faecalis, E. faecium, S. epidermidis and S. hemolyticus, and are particularly useful against strains of methicillin-resistant S. aureus.

The compounds of formula I are characterized by a substituted pyridiniumthiomethyl group of the type at the 3-position of the cephem ring and a lipophilic 7-substituent of the type wherin Ar is an aromatic group selected from optionally substituted phenyl, naphthyl or pyridyl.

To elaborate on the definitions for the substituents of the formula I compounds:

(a) "Halogen" includes chloro, bromo, fluoro and iodo, and is preferably chloro or bromo;

(b) "Trihalomethyl" includes trichloromethyl, trifluoromethyl, tribromomethyl and triiodomethyl, but is preferably trifluoromethyl;

(c) The aliphatic "alkyl" group may be straight or branched chains having the specified number of carbon atoms. It is preferred that such a group have up to 6 carbon atoms and most preferably up to 4 carbon atoms;

(d) The alkyl or cycloalkyl $R^1$ substituent is linked by a carbon atom to the quaternary nitrogen of the pyridine ring, e.g.

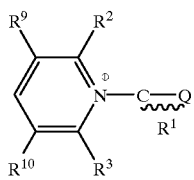

where C—Q represents the $R^1$ substituent.

The term "pharmaceutically acceptable salt" as used herein is intended to include the nontoxic acid addition salts with inorganic or organic acids, e.g. salts with acids such as hydrochloric, phosphoric, sulfuric, maleic, acetic, citric, succinic, benzoic, fumaric, mandelic, p-toluenesulfonic, methanesulfonic, ascorbic, lactic, gluconic, trifluoroacetic, hydroiodic, hydrobromic, and the like. Some of the compounds of the present invention have an acidic hydrogen and can, therefore, be converted with bases in a conventional manner into pharmaceutically acceptable salts. Such salts, e.g. ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl) aminomethane), or with bases such as piperidine or morpholine, are also intended to be encompassed by the term "pharmaceutically acceptable salt".

Compounds of formula I in the form of acid addition salts may be written as

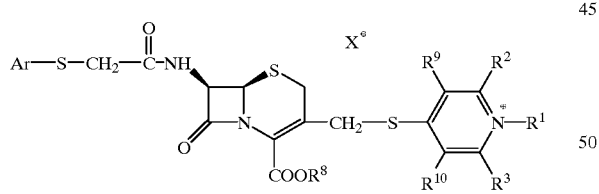

where $X^\ominus$ represents the acid anion and $R^8$ is hydrogen or a carboxyl-protecting group. The counter anion $X^\ominus$ may be selected so as to provide pharmaceutically acceptable salts for therapeutic administration.

The carboxyl-protecting group $R^8$ is intended to include readily removable ester groups which have been conventionally employed to block a carboxyl group during the reaction steps used to prepare compounds I and which can be removed by methods which do not result in any appreciable destruction of the remaining portion of the molecule, e.g. by chemical or enzymatic hydrolysis, treatment with chemical reducing agents under mild conditions, irradiation with ultraviolet light or catalytic hydrogenation, etc. Examples of such protecting groups include benzhydryl, p-nitrobenzyl, 2-naphthylmethyl, allyl, benzyl, p-methoxybenzyl, trichloroethyl, silyl such as trimethylsilyl, phenacyl, acetonyl, o-nitrobenzyl, 4-pyridylmethyl and $(C_1-C_6)$alkyl such as methyl, ethyl or t-butyl. Included within such protecting groups are those which are hydrolyzed under physiological conditions such as pivaloyloxymethyl, acetoxymethyl, phthalidyl, indanyl, α-acetoxyethyl, α-pivaloyloxyethyl, and methoxymethyl. Compounds of formula I with such physiologically hydrolyzable carboxyl protecting groups are also referred to herein and in the claims as "prodrugs". Compounds of formula I where $R^8$ is a physiologically removable protecting group are useful directly as antibacterial agents. Compounds where an $R^8$ protecting group is not physiologically removable are useful intermediates which can be easily converted to the active form by conventional deblocking procedures well-known to those skilled in the art.

Compounds of formula I wherein a hydroxyl substituent is esterified with a group hydrolyzable under physiological conditions are also included within the scope of the term "prodrug" as used herein. Such hydroxyl protecting groups may be employed, for example, to increase the solubility of the formula I compound. Illustrative of suitable ester "prodrugs" of this type are compounds of formula I wherein one or more hydroxy substituent groups are converted to sulfate ($-OSO_3H$) or phosphate ($-OPO_3H_2$) groups.

A preferred embodiment of the present invention comprises compounds of formula I wherein $R^1$ is

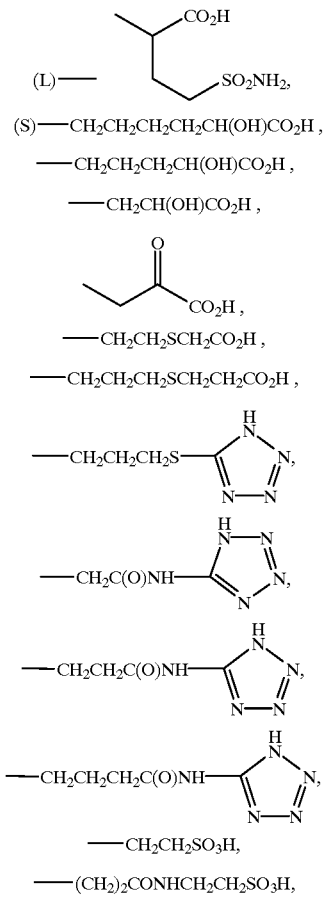

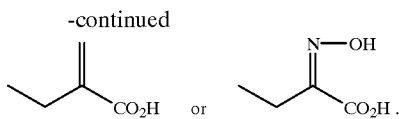

The most preferred Ar substituents for the compounds of the present invention are

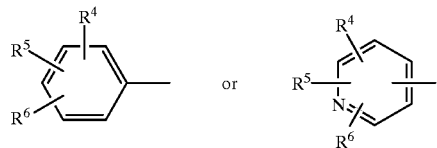

in which $R^4$, $R^5$ and $R^6$ are each independently hydrogen, halogen, $(C_1-C_6)$alkyl, trifluoromethyl, hydroxy, hydroxy $(C_1-C_6)$alkyl or amino.

Another preferred embodiment of the present invention comprises compounds of formula I in which $R^1$ is

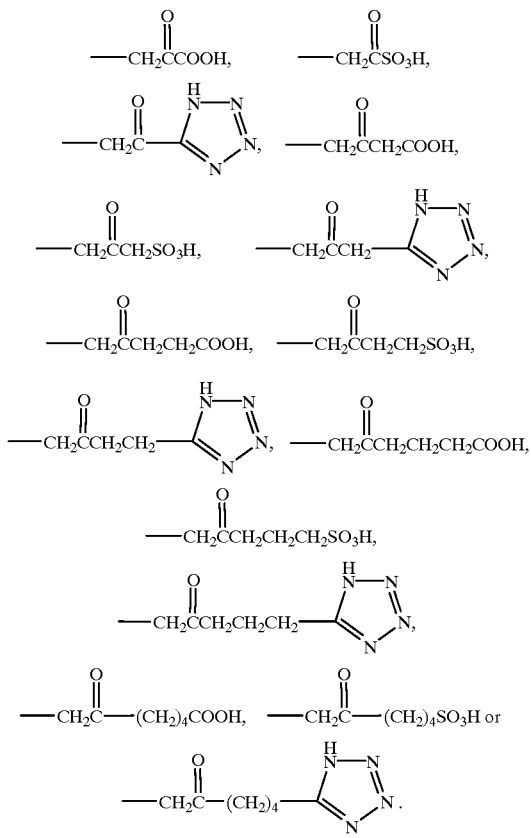

Within this embodiment the preferred Ar substituents are

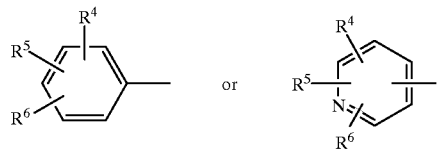

in which $R^4$, $R^5$ and $R^6$ are each independently hydrogen, halogen, $(C_1-C_6)$alkyl, trifluoromethyl, hydroxy, hydroxy $(C_1-C_6)$alkyl or amino. The most preferred Ar substituents are

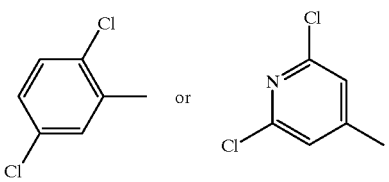

The preferred individual compounds of the present invention, all of which have an MIC vs a representative MRSA strain of $\leq 8$ μg/ml, are listed below:

1-[2-carboxy-2-propen-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 1)

1-[2-carboxy-2-hydroxy ethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 2)

1-(carboxymethyl)-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 3)

1-[(3-carboxy-1-propyl)]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 4)

1-[(5-carboxy-1-pentyl)]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 5)

1-[(R)-1-carboxy-1-ethyl]-4-[[(6R)-trans-2-carboxy-8-oxo-7-[(2,5-dichlorophenylthio)acetamido]-5-thia-1-azabicyclo [4.2.0]-oct-2-en-3-yl]methylthio]pyridinium inner salt or a pharmaceutically acceptable salt thereof (compound of Example 6)

1-[(1-carboxy-1-cyclopropyl)]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 7)

1-[(S)-1-carboxy-2-hydroxy-1-ethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 8)

1-[(1S, 2R, 3S, 4R)-1-carboxy-2,3,4,5-tetrahydroxy pent-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 9)

1-[(S)-1-carboxy-3-(methylthio)prop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 10)

1-[(S)-1-carboxy-3-(methylsulfinyl)prop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]

methylthio]pyridinium inner salt or a pharmaceutically acceptable salt thereof (compound of Example 11)

1-[(S)-1-carboxy-3-(methylsulfonyl)prop-1-yl]-4-[[(6R)-trans-2-carboxy-8-oxo-7-[(2,5-dichlorophenylthio) acetamido]-5-thia-1-azabicyclo[4.2.0]-oct-2-en-3-yl) methylthio]pyridinium inner salt or a pharmaceutically acceptable salt thereof (compound of Example 12)

1-[(S)-3-aminosulfonyl-1-carboxyprop-1-yl]-4-[[(6R)-trans-2-carboxy-8-oxo-7-[(2,5-dichlorophenylthio) acetamido]-5-thia-1-azabicyclo[4.2.0]-oct-2-en-3-yl] methylthio]pyridinium inner salt or a pharmaceutically acceptable salt thereof (compound of Example 13)

1-[(S)-4-(aminocarbonyl)amino-1-carboxybut-1-yl]-4-[[(6R)-trans-2-carboxy-8-oxo-7-[(2,5-dichlorophenylthio) acetamido]-5-thia-1-azabicyclo[4.2.0]-oct-2-en-3-yl] methylthio]pyridinium inner salt or a pharmaceutically acceptable salt thereof (compound of Example 14)

1-[(S)-1-carboxy-(4-hydroxy phenyl)methyl]-4-[[(6R)-trans-2-carboxy-8-oxo-7-[(2,5-dichlorophenylthio) acetamido]-5-thia-1-azabicyclo[4.2.0]-oct-2-en-3-yl] methylthio]pyridinium inner salt or a pharmaceutically acceptable salt thereof (compound of Example 15)

1-[(S)-1-carboxy-2-(2-thienyl)ethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio] pyridinium inner salt or a pharmaceutically acceptable salt thereof (compound of Example 16)

1-[3-carboxy-2-hydroxy-1-propyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio] pyridinium inner salt or a pharmaceutically acceptable salt thereof (compound of Example 17)

1-[(S)-5-carboxy-5-hydroxypent-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio] pyridinium inner salt or a pharmaceutically acceptable salt thereof (compound of Example 18)

1-[(S)-5-carboxy-5-hydroxypent-1-yl]-4-[[(6R)-trans-2-carboxy-8-oxo-7-[(2,6-dichloropyridin-4-yl) thioacetamido]-5-thia-1-azabicyclo[4.2.0]-oct-2-en-3-yl] methylthio]pyridinium inner salt or a pharmaceutically acceptable salt thereof (compound of Example 19)

1-[(S)-4-carboxy-4-hydroxybut-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio] pyridinium inner salt or a pharmaceutically acceptable salt thereof (compound of Example 20)

1-[(S)-4-carboxy-4-hydroxybut-1-yl]-4-[[(6R)-trans-2-carboxy-8-oxo-7-[(2,6-dichloropyridin-4-yl) thioacetamido]-5-thia-1-azabicyclo[4.2.0]-oct-2-en-3-yl] methylthio]pyridinium inner salt or a pharmaceutically acceptable salt thereof (compound of Example 21)

1-[(R)-4-carboxy-4-hydroxybut-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio] pyridinium inner salt or a pharmaceutically acceptable salt thereof (compound of Example 22)

1-[(R)-4-carboxy-4-hydroxybut-1-yl]-4-[[(6R)-trans-2-carboxy-8-oxo-7-[(2,6-dichloropyridin-4-yl) thioacetamido]-5-thia-1-azabicyclo[4.2.0]-oct-2-en-3-yl] methylthio]pyridinium inner salt or a pharmaceutically acceptable salt thereof (compound of Example 23)

1-[(S)-3-carboxy-3-hydroxyprop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio] pyridinium inner salt or a pharmaceutically acceptable salt thereof (compound of Example 24)

1-[(S)-3-carboxy-3-hydroxyprop-1-yl]-4-[[(6R)-trans-2-carboxy-8-oxo-7-[(2,6-dichloropyridin-4-yl) thioacetamido]-5-thia-1-azabicyclo [4.2.0]-oct-2-en-3-yl] methylthio]pyridinium inner salt or a pharmaceutically acceptable salt thereof (compound of Example 25)

1-[2-carboxy-2-hydroxy ethyl]-4-[[(6R)-trans-2-carboxy-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof (compound of Example 26)

1-[(S)-3-carboxy-3-hydroxy-2,2-dimethylprop-1-yl]-4-[[(6R)-trans-2-carboxy-8-oxo-7-[(2,5-dichlorophenylthio) acetamido]-5-thia-1-azabicyclo[4.2.0]-oct-2-en-3-yl] methylthio]pyridinium inner salt or a pharmaceutically acceptable salt thereof (compound of Example 27)

1-[(2R,3R)-3-carboxy-2,3-dihydroxyprop-1-yl]-4-[[(6R)-trans-2-carboxy-8-oxo-7-[[(2,5-dichlorophenylthio) acetamido]-5-thia-1-azabicyclo[4.2.0]-oct-2-en-3-yl] methylthio]pyridinium inner salt or a pharmaceutically acceptable salt thereof (compound of Example 28)

1-[(2,2-dimethyl-4-carboxydioxolan-5-yl)methyl]-4-[[(6R)-trans-2-carboxy-8-oxo-7-[(2,5-dichlorophenylthio) acetamido]-5-thia-1-azabicyclo[4.2.0]-oct-2-en-3-yl] methylthio]pyridinium inner salt or a pharmaceutically acceptable salt thereof (compound of Example 29)

1-[2-carboxy-2-oxoeth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 30)

1-[2-carboxy-2-oxoeth-1-yl]-4-[[(6R)-trans-2-carboxy-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof (compound of Example 31)

1-[3-carbomethoxy-2-oxoprop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio] pyridinium inner salt or a pharmaceutically acceptable salt thereof (compound of Example 32)

1-[4-carboxy-2-oxoprop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 33)

1-[2,2-dimethyl-3-carboxy-3-oxoprop-1-yl]-4-[[(6R)-trans-2-carboxy-8-oxo-7-[(2,5-dichlorophenylthio) acetamido]-5-thia-1-azabicyclo[4.2.0]-oct-2-en-3-yl] methylthio]pyridinium inner salt or a pharmaceutically acceptable salt thereof (compound of Example 34)

1-[2-carboxy-2-fluoroeth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 35)

1-[3-carboxy-3-fluoroprop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio] pyridinium inner salt or a pharmaceutically acceptable salt thereof (compound of Example 36)

1-[3-carboxy-3,3-difluoroprop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio] pyridinium inner salt or a pharmaceutically acceptable salt thereof (compound of Example 37)

1-[2-(carboxymethylthio)eth-1-yl]-4-[[(6R)-trans-2-carboxy-8-oxo-7-[(2,5-dichlorophenylthio)acetamido]-5- thia-1-azabicyclo[4.2.0]1-oct-2-en-3-yl]methylthio]pyridinium inner salt or a pharmaceutically acceptable salt thereof (compound of Example 38)

1-[3-(2-carboxyethylthio)-1-propyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 39)

1-[N-(carboxymethyl)-aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 40)

1-[N-(carboxymethyl)-aminocarbonylmethyl]-4-[[(6R)-trans-2-carboxy-8-oxo-7-[(2,4,5-trichlorophenylthio)acetamido]-5-thia-1-azabicyclo[4.2.0]-oct-2-en-3-yl]methylthio]pyridinium inner salt or a pharmaceutically acceptable salt thereof (compound of Example 41)

1-[N-(carboxymethyl)-aminocarbonylmethyl]-4-[[(6R)-trans-2-carboxy-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof (compound of Example 42)

1-[N-(2-carboxyethyl)-aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 43)

1-[N-(2-carboxyethyl)-aminocarbonylmethyl]-4-[[(6R)-trans-2-carboxy-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof (compound of Example 44)

1-[N-(2-carboxyethyl-2-hydroxy)aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 45)

1-[N-(1-carboxy-2-hydroxyeth-1-yl)aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 46)

1-[N-(1-carboxy-2-hydroxyeth-1-yl)aminocarbonylmethyl]-4-[[(6R)-trans-2-carboxy-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof (compound of Example 47)

1-[N-(1-carboxy-3-methylthioprop-1-yl)aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 48)

1-[2-((S)-N-prolyl)-2-oxoeth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 49)

1-[N-(1-carboxy-2-phenylethyl)aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 50)

1-[N-(1-carboxy-2-(4-hydroxyphenyl)ethyl)aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 51)

1-[N-(1-carboxy-2-histidylethyl)aminocarbonylmethyl]-4-[[(6R)-trans-2-carboxy-8-oxo-7-[(2,5-dichlorophenylthio)acetamido]-5-thia-1 -azabicyclo[4.2.0]-oct-2-en-3-yl]methylthio]pyridinium inner salt or a pharmaceutically acceptable salt thereof (compound of Example 52)

1-[N-(carboxymethyl)-1-aminocarbonyleth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 53)

1-[N-methyl-N-(carboxymethyl)aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a =pharmaceutically acceptable salt thereof (compound of Example 54)

1-(sulfomethyl)-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 55)

1-(2-sulfoeth-1-yl)-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 56)

2,6-dimethyl-1-(2-sulfoeth-1-yl)-4-[[(6R)-trans-2-carboxy-8-oxo-7-[(2,5-dichlorophenylthio)acetamido]-5-thia-1-azabicyclo [4.2.0]-oct-2-en-3-yl]methylthio]pyridinium inner salt or a pharmaceutically acceptable salt thereof (compound of Example 57)

2-ethyl-i-(2-sulfoethyl)-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 58)

2,3-dimethyl-1-(2-sulfoethyl)-4-[[(6R)-trans-2-carboxy-8-oxo-7-[(2,5-dichlorophenylthio)acetamido]-5-thia-1-azabicyclo [4.2.0]-oct-2-en-3-yl]methylthio]pyridinium inner salt or a pharmaceutically acceptable salt thereof (compound of Example 59)

1-[N-(2-sulfoethyl)aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 60)

1-[N-(2-sulfoethyl)aminocarbonylmethyl]-4-[[(6R)-trans-2-carboxy-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof (compound of Example 61)

1-[N-(2-sulfoethyl)-2-aminocarbonylethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 62)

1-[N-(2-sulfoethyl)-2-aminocarbonylethyl]-4-[[(6R)-trans-2-carboxy-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof (compound of Example 63)

1-[3-(5-tetrazolylthio)prop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 64)

1-[N-(5-tetrazolyl)aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 65)

1-[N-(5-tetrazolyl)-2-aminocarbonyleth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 66)

1-[N-(5-tetrazolyl)-3-aminocarbonylprop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 67)

1-[2-carboxy-2-(hydroxyimino)eth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 68)

1-[N-methyl-N-(3-carboxy-1-oxoprop-1-yl)-2-aminoeth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 69)

1-[1-carboxy-2-hydroxy-2-(2-thienyl)eth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 70)

1-[N-(2-carboxy-1-oxoeth-1-yl)-2-aminoeth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 71); and 1-[2-(2-sulfoethylthio)eth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 72).

The more preferred individual compounds of the present invention, all of which have a MIC≦8 μg/mL are listed below:

1-[2-carboxy-2-propen-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 1)

1-[2-carboxy-2-hydroxy ethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 2)

1-[(R)-1-carboxy-1-ethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 6)

1-[(S)-1-carboxy-3-(methylsulfinyl)prop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 11)

1-[(S)-1-carboxy-3-(methylsulfonyl)prop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 12)

1-[(S)-3-aminosulfonyl-1-carboxyprop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 13)

1-[(S)-5-carboxy-5-hydroxypent-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 18)

1-[(S)-4-carboxy-4-hydroxybut-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 20)

1-[(R)-4-carboxy-4-hydroxybut-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 22)

1-[(S)-3-carboxy-3-hydroxyprop-1-yl]-4-[[(6R)-trans-2-carboxy-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof (compound of Example 25)

1-[2-carboxy-2-hydroxy ethyl]-4-[[(6R)-trans-2-carboxy-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof (compound of Example 26)

1-[2-carboxy-2-oxoeth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 30)

1-[2-carboxy-2-oxoeth-1-yl]-4-[[(6R)-trans-2-carboxy-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof (compound of Example 31)

1-[3-carbomethoxy-2-oxoprop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 32)

1-[2-(carboxymethylthio)eth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 38)

1-[3-(2-carboxyethylthio)-1-propyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 39)

1-[N-(carboxymethyl)-aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 40)

1-[N-(carboxymethyl)-aminocarbonylmethyl]-4-[[(6R)-trans-2-carboxy-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof (compound of Example 42)

1-[N-(2-carboxyethyl)-aminocarbonylmethyl]-4-[[(6R)-trans-2-carboxy-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof (compound of Example 44)

1-[N-(1-carboxy-2-phenylethyl)aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 50)

1-(sulfomethyl)-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 55)

1-(2-sulfoeth-1-yl)-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 56)

2,6-dimethyl-1-(2-sulfoeth-1-yl)-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 57)

2-ethyl-1-(2-sulfoethyl)-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 58)

2,3-dimethyl-1-(2-sulfoethyl)-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 59)

1-[N-(2-sulfoethyl)aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 60)

1-[N-(2-sulfoethyl)-2-aminocarbonylethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 62)

1-[N-(2-sulfoethyl)-2-aminocarbonylethyl]-4-[[(6R)-trans-2-carboxy-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof (compound of Example 63)

1-[3-(5-tetrazolylthio)prop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 64)

1-[N-(5-tetrazolyl)aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 65)

1-[N-(5-tetrazolyl)-2-aminocarbonyleth-1-yl]-4-[[(6R)-trans-2-carboxy-8-oxo-7-[(2,5-dichlorophenylthio)acetamido]-5-thia-1-azabicyclo[4.2.0)-oct-2-en-3-yl]methylthio]pyridinium inner salt or a pharmaceutically acceptable salt thereof (compound of Example 66)

1-[N-(5-tetrazolyl)-3-aminocarbonylprop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 67)

1-[2-carboxy-2-(hydroxyimino)eth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 68)

1-[1-carboxy-2-hydroxy-2-(2-thienyl)eth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 70); and 1-[2-(2-sulfoethylthio)eth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 72).

The most preferred individual compounds of the present invention are listed below:

1-[2-carboxy-2-propen-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 1)

1-[2-carboxy-2-hydroxy ethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 2)

1-[(S)-3-aminosulfonyl-1-carboxyprop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 13)

1-[(S)-5-carboxy-5-hydroxypent-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 18)

1-[(S)-4-carboxy-4-hydroxybut-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 20)

1-[(R)-4-carboxy-4-hydroxybut-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 22)

1-[(S)-3-carboxy-3-hydroxyprop-1-yl]-4-[[(6R)-trans-2-carboxy-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof (compound of Example 25)

1[2-carboxy-2-oxoeth-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 30)

1-[2-carboxy-2-oxoeth -1-yl]-4-[[(6R) -trans-2-carboxy-8-oxo-7-[(2,6-dichloropyridin-4-yl)thioacetamido]-5-thia- 1-azabicyclo[4.2.0]-oct-2-en-3-yl]methylthio]pyridinium inner salt or a pharmaceutically acceptable salt thereof (compound of Example 31)

1-[2-(carboxymethylthio)eth-1-yl]-4-[[(6R) -trans-2-carboxy-8-oxo-7-[(2,5-yl]methylthio]pyridinium inner salt or a pharmaceutically acceptable salt thereof (compound of Example 38)

1-[3-(2-carboxyethylthio)-1-propyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio] pyridinium inner salt or a pharmaceutically acceptable salt thereof (compound of Example 39)

1-[N-(2-carboxyethyl)-aminocarbonylmethyl]-4-[[(6R)-trans-2-carboxy-8-oxo-7-[(2,6-dichloropyridin-4-yl)thioacetamido]-5-thia-1-azabicyclo[4.2.0]-oct-2-en-3-yl] methylthio]pyridinium inner salt or a pharmaceutically acceptable salt thereof (compound of Example 44)

1-(2-sulfoeth-1-yl)-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 56)

2,6-dimethyl-1-(2-sulfoeth-1-yl)-4-[[(6R)-trans-2-carboxy-8-oxo-7-[(2,5-dichlorophenylthio)acetamido]-5-thia-1-azabicyclo[4.2.0]-oct-2-en-3-yl]methylthio] pyridinium inner salt or a pharmaceutically acceptable salt thereof (compound of Example 57)

2,3-dimethyl-1-(2-sulfoethyl)-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof (compound of Example 59)

1-[N-(2-sulfoethyl)-2-aminocarbonylethyl]-4-[[(6R)-trans-2-carboxy-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof (compound of Example 62)

1-[N-(2-sulfoethyl)-2-aminocarbonylethyl]-4-[[(6R)-trans-2-carboxy-8-oxo-7-[(2,6-dichloropyridin-4-yl)thioacetamido]-5-thia-1-azabicyclo[4.2.0]-oct-2-en-3-yl] methylthio]pyridinium inner salt or a pharmaceutically acceptable salt thereof (compound of Example 63)

1-[3-(5-tetrazolylthio)prop-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio] pyridinium inner salt or a pharmaceutically acceptable salt thereof (compound of Example 64)

1-[N-(5-tetrazolyl)aminocarbonylmethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio] pyridinium inner salt or a pharmaceutically acceptable salt thereof (compound of Example 65)

1-[N-(5-tetrazolyl)-2-aminocarbonyleth-1-yl]-4-[[(6R)-trans-2-carboxy-8-oxo-7-[(2,5-dichlorophenylthio) acetamido]-5-thia-1-azabicyclo[4.2.0]-oct-2-en-3-yl] methylthio]pyridinium inner salt or a pharmaceutically acceptable salt thereof (compound of Example 66)

1-[N-(5-tetrazolyl)-3-aminocarbonylprop-1-yl]-4-[[(6R)-trans-2-carboxy-8-oxo-7-[(2,5-dichlorophenylthio) acetamido]-5-thia-1-azabicyclo[4.2.0]-oct-2-en-3-yl] methylthio]pyridinium inner salt or a pharmaceutically acceptable salt thereof (compound of Example 67); and 1-[2-carboxy-2-(hydroxyimino)eth-1-yl-4-[[(6 R)-trans-2-carboxy-8-oxo-7-[(2,5-dichlorophenylthio)acetamido]-5-thia-1-azabicyclo[4.2.0]-oct-2-en-3-yl]methylthio] pyridinium inner salt or a pharmaceutically acceptable salt thereof (compound of Example 68).

The compounds of the present invention can be made by conventional methods. Two suitable procedures are summarized in the following reaction scheme:

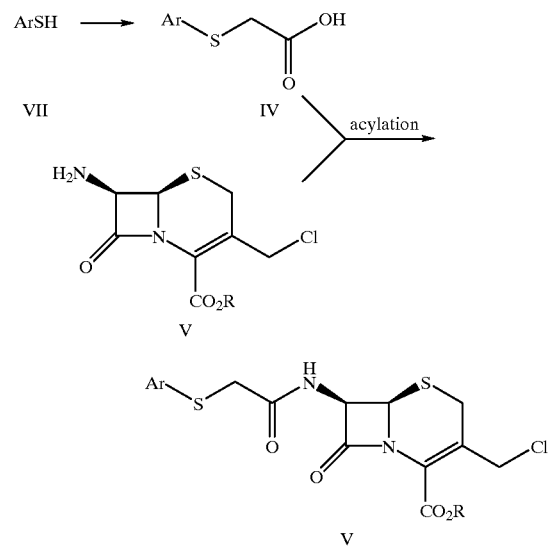

R = ester protecting group such as diphenylmethyl (DPM) or para-methoxybenzyl (PMB)

Method 1

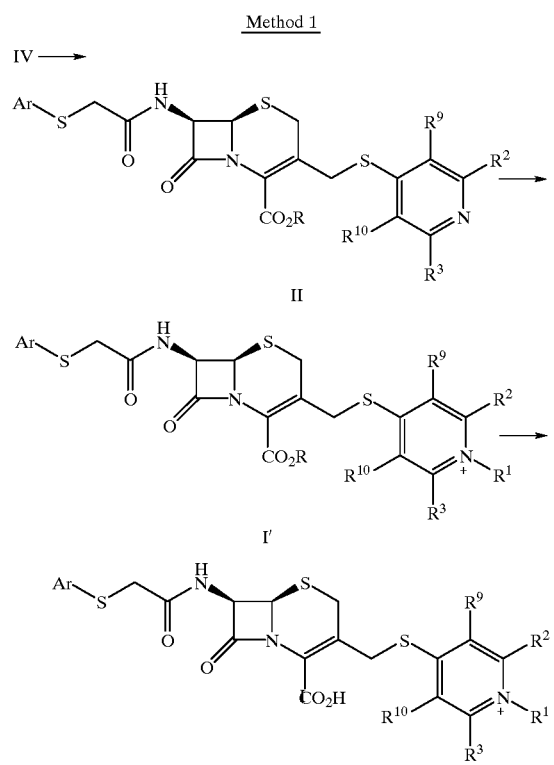

Method 2

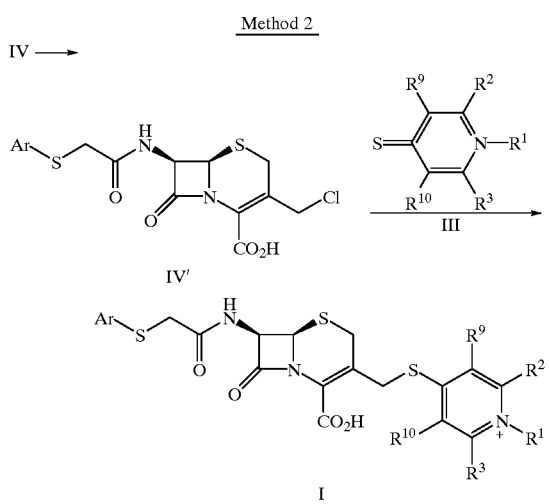

To elaborate on the above process, thiol VII is converted into the arylthioacetic acid derivative VI by treatment with bromoacetic acid under basic conditions (e.g. aqueous sodium or potassium hydroxide). The reaction temperature for this step is typically between 20° C. and 100° C. Starting thiol VII is commercially available or can be prepared according to known literature procedures. Following acidification of the reaction mixture, the product VI is typically isolated by crystallization or, if necessary, it can be purified by chromatography.

Arylthioacetic acid VI is then coupled with a suitable cephem intermediate having a 3-substituent leaving group. For example, the leaving group may be acetoxy or halo. In the preferred embodiment illustrated by the reaction scheme, the cephem intermediate is the 3chloro cephem V, but other suitable cephem intermediates with equivalent leaving groups at the 3-position could also be employed. The cephem intermediate V may be acylated with VI or a reactive derivative thereof by conventional acylation procedures well-known in the cephalosporin art to give N-acylated intermediate IV. In addition to using the free arylthioacetic acid, e.g. with a suitable condensing agent such as dicyclohexylcarbodiimide, acylating agent VI may also be employed in the form of equivalent acylating derivatives such as an acid anhydride, mixed anhydride, activated ester, or acid halide. The cephem intermediate preferably has the carboxyl group protected by a conventional carboxyl-protecting group which can be readily removed. Examples of such protecting groups are discussed above and include benzyl, 4-nitrobenzyl, 4-methoxybenzyl, diphenylmethyl, allyl, and the like. Other examples of suitable protecting groups are disclosed in *Protective Groups in Organic Synthesis,* Theodora W. Greene (John Wiley & Sons, 1981), Chapter 5. In one embodiment, intermediate V may be acylated with acid VI in the presence of dicyclohexylcarbodiimide and in an inert solvent such as tetrahydrofuran or dichloromethane. The reaction temperature is typically between −20° C. and 50° C. Upon completion of the reaction, insoluble material is removed by filtration, the filtrate is concentrated, and the residue is treated with a relatively non-polar solvent such as diethyl ether or ethyl acetate resulting in precipitation of the desired product. Alternatively, acid VI may be converted to the corresponding acid chloride, for example by treatment with thionyl chloride with or without a solvent such as dichloromethane, followed by coupling with cephem amine V in the presence of a base such as triethylamine or N-methylmorpholine to give intermediate IV. Cephem IV is typically isolated after aqueous work-up and evaporation of volatile solvents followed by trituration of the compound with a relatively non-polar solvent such as diethyl ether or ethyl acetate. This intermediate may be used in the next reaction step as the X=chloride derivative, or can be converted to the X=bromide or X=iodide derivative by treatment with the appropriate metal halide in a solvent such as acetone.

Conversion of cephem IV to the target quaternary cephems I is accomplished by two different methods. One method for preparation of I entails displacement of an appropriate 3-substituent leaving group with 4-mercaptopyridine followed by quaternization of the pyridyl nitrogen, and then deprotection of the cephem carboxylate ester. For example, cephem IV (X=Cl) is treated with optionally substituted 4-mercaptopyridine and sodium iodide in a one-pot reaction to give intermediate II. Reaction of thiopyridyl derivative II with a reactive alkylating agent provides the quaternary cephem intermediate I'. Examples of alkylating agents are α-halocarbonyl derivatives such as N-substituted haloacetamides. The alkylation reaction is carried out in an inert solvent such as acetone, dimethylformamide, or tetrahydrofuran and is run at temperatures between −20° C. and 100° C. Removal of the cephem carboxylate ester protecting group to give I is then accomplished under acidic conditions. For example, when R is diphenylmethyl or 4-methoxybenzyl, I is obtained upon treatment of I' with trifluoroacetic acid neat or in an inert solvent such as methylene chloride. A reagent such as anisole may also be employed to scavenge the liberated ester protecting group. The reaction temperature is usually at or below room temperature. The deprotection may also be carried out by treatment with other protic acids such as hydrochloric acid in a solvent such as methanol. The final product is typically isolated by precipitation or crystallization. In some cases, cephem I is purified by column chromatography, for example on reversed-phase adsorbent.

In a second method of preparing quaternary cephems I, intermediate IV is deprotected under acidic conditions, followed by reaction of the resulting intermediate IV' with a thiopyridone derivative m. For example, when R is diphenylmethyl or 4methoxybenzyl, cephem acid IV' is obtained upon treatment of IV with trifluoroacetic acid neat or in an inert solvent such as methylene chloride. A reagent such as anisole may also be employed to scavenge the liberated ester protecting group. The reaction temperature is usually at or below room temperature. The deprotection may also be carried out by treatment with other protic acids such as hydrochloric acid in a solvent such as methanol. The final product is typically isolated by precipitation or crystallization. Reaction of IV' with a thiopyridone derivative III in a solvent such as dimethylformamide, dimethyl sulfoxide, ethanol, methanol, or other appropriate solvents at a temperature between −20° C. and 100° C. affords target quaternary cephem I. The final product is isolated as described above. Thiopyridones III are typically prepared according to a method analogous to that described in T. Takahashi et al., European Patent Application No. 209751 and in I. E. El-Kholy et al., J. Heterocyclic Chem. Vol. 11, p. 487 (1974). This procedure entails reaction of 4-thiopyrone (European Patent No. 209751) with an appropriate primary amine in a solvent such as aqueous methanol or ethanol at a temperature ranging between 0° C. and 78° C. The primary amine may be in the form of a zwitterion in examples where there is a free acid group present in the molecule. In these cases, a base such as sodium hydroxide, sodium bicarbonate, or pyridine is added to form the free amine in situ. The product may be isolated as its sodium salt by evaporation of volatile solvents, followed by trituration with a solvent such as diethyl ether or ethyl acetate. Alternatively, the reaction mixture may be acidified and extracted with an organic solvent to afford the product as the free carboxylic acid. If the carboxylate group is protected as an ester, the amine may be free or present as an acid salt. In the latter case, a base such as sodium hydroxide, sodium bicarbonate, or pyridine is added to form the free amine in situ. The product is typically isolated by precipitation or by reverse phase column chromatography following removal of volatile solvents.

The thiopyridone derivatives of formula III are another aspect of the present invention. The preferred $R^1$, $R^2$, $R^3$, $R^9$ and $R^{10}$ substituents of derivatives III are as disclosed above in connection with the end-products of formula I.

It will be understood that where the substituent groups used in the above reactions contain certain reaction-sensitive functional groups such as carboxylate groups which might result in undesirable side-reactions, such groups may be protected by conventional protecting groups known to those skilled in the art. Suitable protecting groups and methods for their removal are illustrated, for example, in *Protective Groups in Organic Synthesis,* Theodora W. Greene (John Wiley & Sons, 1991). It is intended that such "protected" intermediates and end-products are included within the scope of the present disclosure and claims.

The desired end-product of formula I may be recovered either as the zwitterion or in the form of a pharmaceutically acceptable acid addition salt, e.g. by addition of the appropriate acid such as HCl, HI or methanesulfonic acid to the zwitterion. Compounds of formula I where $R^8$ is hydrogen, an anionic charge or a pharmaceutically acceptable salt thereof may be converted by conventional procedures to a corresponding compound where $R^8$ is a physiologically hydrolyzable ester group.

It will be appreciated that certain products within the scope of formula I may have a C-3 substituent group which can result in formation of optical isomers. It is intended that the present invention include within its scope all such optical isomers as well as epimeric mixtures thereof, i.e. R— or S— or racemic forms.

The novel cephalosporin derivatives of general formula I wherein $R^8$ is hydrogen, an anionic charge or a physiologically hydrolyzable carboxyl-protecting group, or the pharmaceutically acceptable salts or prodrugs thereof, are potent antibiotics active against many gram-positive bacteria. While they may be used, for example, as animal feed additives for promotion of growth, as preservatives for food, as bactericides in industrial applications, for example in waterbased paint and in the white water of paper mills to inhibit the growth of harmful bacteria, and as disinfectants for destroying or inhibiting the growth of harmful bacteria on medical and dental equipment, they are especially useful in the treatment of infectious disease in humans and other animals caused by the gram-positive bacteria sensitive to the new derivatives. Because of their excellent activity against MRSA organisms, they are particularly useful in the treatment of infections resulting from such bacteria.

The pharmaceutically active compounds of this invention may be used alone or formulated as pharmaceutical compositions comprising, in addition to the active cephem ingredient, a pharmaceutically acceptable carrier or diluent. The compounds may be administered by a variety of means, for example, orally, topically or parenterally (intravenous or intramuscular injection). The pharmaceutical compositions may be in solid form such as capsules, tablets, powders, etc. or in liquid form such as solutions, suspensions or emulsions. Compositions for injection, the preferred route of delivery, may be prepared in unit dose form in ampules or in multidose containers and may contain additives such as suspending, stabilizing and dispersing agents. The compositions may be in ready-to-use form or in powder form for reconstitution at the time of delivery with a suitable vehicle such as sterile water.

The dosage to be administered depends, to a large extent, on the particular compound being used, the particular composition formulated, the route of administration, the nature and condition of the host and the particular situs and organism being treated. Selection of the particular preferred dosage and route of application, then, is left to the discretion of the physician or veterinarian. In general, however, the compounds may be administered parenterally or orally to mammalian hosts in an amount of from about 50 mg/day to about 20 g/day. Administration is generally carried out in divided doses, e.g., three to four times a day, analogous to dosing with a cephalosporin such as cefotaxime.

IN VITRO ACTIVITY

Samples of the compounds prepared below in Examples 1–72 after solution in water and dilution with Nutrient Broth were found to exhibit the following ranges of Minimum Inhibitory Concentrations (MIC) versus the indicated microorganisms as determined by tube dilution. The MICs were determined using a broth micro dilution assay in accordance with that recommended by the National Committee for Clinical Laboratory Standards (NCCLS). Mueller-Hinton medium was used except for Streptococci which was tested in Todd Hewitt broth. The final bacterial inoculate contained approximately $5\times10^5$ cfu/ml and the plates were incubated at 35° C. for 18 hours in ambient air (Streptococci in 5% $CO_2$). The MIC was defined as the lowest drug concentration that prevented visible growth.

| Microorganism | MIC range in ug/ml |
| --- | --- |
| S. aureus methicillin resistant A27223 | 1–8 |
| S. pneumoniae A9585 | 0.0005–2 |
| S. pyogenes A9604 | 0.0005–2 |
| E. faecalis A20688 | 0.25–8 |
| E. faecium A24885 | 0.5–16 |
| S. aureus A9537, penicillinase negative | 0.0005–0.125 |
| S. aureus A15090, penicillinase positive | 0.03–1 |
| S. epidermidis A24548 | 0.001–1 |
| S. epidermidis A25783, methicillin resistant | 0.015–2 |
| S. hemolyticus A21638 | 0.015–8 |
| S. hemolyticus A27235, methicillin resistant | 0.25–32 |

IN VIVO ACTIVITY

The in vivo therapeutic efficacy of the compounds prepared in Examples 1–72 below after intramuscular injection to mice experimentally infected with the representative MRSA strain A27223 was also measured.

The determination of the effectiveness of antimicrobial agents in *Staphylococcus aureus* systemic infection in mice Organisms: The test organism, MRSA strain A27223 used to generate systemic infection in mice, is grown on two large Brain Heart Infusion Agar plates. On each plate, 0.5 ml of frozen stock culture is plated out. Plates are then incubated for 18 hours at 30° C. The next day each plate is washed with 20 ml of Brain Heart Infusion Broth and then pooled together. A microscopic direct count of microorganism is done using a 1:1000 dilution of plate wash. After a direct count is obtained, the number of organisms per milliliter is calculated. The count is adjusted to the desired amount of inoculum by diluting in 4% hog mucin. The desired challenge (amount of organisms given to mice) is 2.4×10⁸ cfu/0.5 ml/mouse for MRSA strain A27223. The mice are infected intraperitoneally with 0.5 ml of challenge. Ten non-treated infected mice are used as controls.

Mice: Mice used are male ICR mice. The average weight of the animals is from 20 to 26 grams.

Drug preparation and treatment: Compounds are tested at 4 dose levels, (25, 6.25, 1.56, and 0.39 mg/kg) and prepared in 5% cremophor, unless otherwise specified. Vancomycin is used as the control compound, and is dosed at 6.25, 1.56, 0.39, and 0.098 mg/kg. It is prepared in 0.1M phosphate buffer. There are five infected mice per dose level, and they are treated with 0.2 ml of the test compound, preferably by intramuscular injection. Treatment begins 15 minutes and 2 hours post-infection.

Test duration: A $PD_{50}$ (the dose of drug given which protects 50% of mice from mortality) runs for 5 days. During this time, mortality of mice are checked every day and deaths are recorded. The cumulative mortality at each dose level is used to calculate a $PD_{50}$ value for each compound. Surviving mice are sacrificed at the end of day 5 by $CO_2$ inhalation.

Calculation: Actual calculation of $PD_{50}$ is performed with a computer program using the Spearman-Karber procedure.

Results: The in vivo efficacy, expressed as the $PD_{50}$ value, ranged from about 0.8 to 22 mg/kg (for certain compounds, more than one test was carried out; the indicated range is for at least one test result when multiple tests were done).

ILLUSTRATIVE EXAMPLES

The following examples illustrate the invention, but are not intended as a limitation thereof. The abbreviations used in the examples are conventional abbreviations well-known to those skilled in the art. Some of the abbreviations used are as follows:

| | | |
|---|---|---|
| h | = | hour(s) |
| mol | = | mole(s) |
| mmol | = | mmole(s) |
| g | = | gram(s) |
| THF | = | tetrahydrofuran |
| L | = | liter(s) |
| mL | = | milliliter(s) |
| Et₂O | = | diethyl ether |
| EtOAc | = | ethyl acetate |

| | | |
|---|---|---|
| MeOH | = | methanol |
| DMF | = | dimethylformamide |

In the following examples, all temperatures are given in degrees Centigrade. Melting points were determined on an electrothermal apparatus and are not corrected. Proton and carbon-13 nuclear magnetic resonance ($^1$H and $^{13}$C NMR) spectra were recorded on a Bruker AM-300 or a Varian Gemini 300 spectrometer. All spectra were determined in $CDCl_3$, DMSO-$d_6$, $CD_3OD$, or $D_2O$ unless otherwise indicated. Chemical shifts are reported in δ units relative to tetramethylsilane (TMS) or a reference solvent peak and interproton coupling constants are reported in Hertz (Hz). Splitting patterns are designated as follows: s, singlet; d, doublet; t, triplet; q, quartet; m, multiplet; br, broad peak; dd, doublet of doublets; dt, doublet of triplets; and app d, apparent doublet, etc. Infrared spectra were determined on a Perkin-Elmer 1800 FT-IR spectrometer from 4000 cm$^{-1}$ to 400 cm$^{-1}$, calibrated to 1601 cm$^{-1}$ absorption of a polystyrene film, and are reported in reciprocal centimeters (cm$^{-1}$). Mass spectra were recorded on a Kratos MS-50 or a Finnegan 4500 instrument utilizing direct chemical ionization (DCI, isobutene), fast atom bombardment (FAB), or electron ion spray (ESI). Ultraviolet spectra were determined on a Hewlett Packard 8452 diode array spectrophotometer in the solvent indicated.

Analytical thin-layer chromatography (TLC) was carried out on precoated silica gel plates (60F-254) and visualized using UV light, iodine vapors, and/or staining by heating with methanolic phosphomolybdic acid. Column chromatography, also referred to as flash chromatography, was performed in a glass column using finely divided silica gel at pressures somewhat above atmospheric pressure with the indicated solvents. Reversed-phase analytical thin-layer chromatography was carried out on precoated reverse phase plates and visualized using UV light or iodine vapors. Reversed-phase column chromatography was performed in a glass column using Baker Octadecyl ($C_{18}$), 40 μm.

Example 1

1-[2-carboxy-2-propen-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium bromide

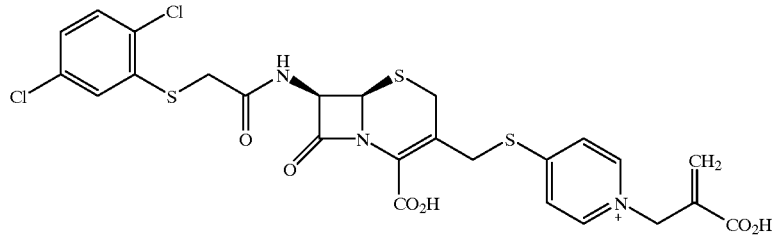

A. 2,5-Dichlorophenylthioacetic acid

A mixture of 2,5-dichlorothiophenol (10.3 g, 57.5 mmol) and bromoacetic acid (8.03 g, 57.8 mmol) in water (225 mL) was treated with 10 N NaOH (13 mL, 130 mmol) and the mixture was heated at 100° C. for 1 h. The reaction mixture was then cooled to 0° C. and acidified to pH 1 with 6N HCl. The product precipitated and was collected by filtration to give 13.0 g (95% yield) of 2,5-dichlorophenylthioacetic acid as white crystals, m.p. 118° C. $^1$H NMR (300 MHz, CDCl$_3$) δ3.74 (s, 2H), 7.15 (dd, J=2, 9 Hz, 1H), 7.32 (d, J=9 Hz, 1H), 7.36 (d, J=2 Hz, 1H). Anal. Calcd. for C$_8$H$_6$O$_2$SCl$_2$: C, 40.53; H, 2.55. Found: C, 40.46; H, 2.64.

B. (6R)-trans-3-Chloromethyl-7-f(2,5-dichlorophenyl) thioacet-amido]-8-oxo-5-thia-1-azabicyclo[4.2.0]oct-2-ene-2-carboxylate, diphenylmethyl ester Method a: A solution of 2,5-dichlorophenylthioacetic acid (13.0 g, 54.9 mmol) in methylene chloride (55 mL) and thionyl chloride (10 mL, 137 mmol) was heated at reflux for 3 h. The reaction mixture was allowed to cool to room temperature and was concentrated in vacuo. The residue was evaporated two times from toluene to give 14 g of 2,5 -dichlorophenylthioacetyl chloride (100% yield) as a slightly colored product which was used in the next step without purification. $^1$H NMR (300 MHz, CDCl$_3$) δ4.13 (s, 2H), 7.22 (dd, J=2, 9 Hz, 1H), 7.35 (d, J=9 Hz, 1H), 7.39 (d, J=2 Hz, 1H).

(6R)-trans-3-Chloromethyl-7-amino-8-oxo-5-thia-1-azabicyclo-[4.2.0]oct-2-ene-2-carboxylate, diphenylmethyl ester, HCl salt was stirred in a biphasic mixture of EtOAc and saturated NaHCO$_3$ for 0.5 h. The layers were separated, and the organic solution was dried over anhydrous MgSO$_4$, filtered, and concentrated to dryness. The free base (9.15 g, 22.0 mmol) was dissolved in THF (200 mL), cooled to 0° C., and treated with N-methylmorpholine (3.34 g, 33.0 mmol) and 2,5-dichlorophenylthioacetyl chloride (6.75 g, 26.4 mmol). The reaction mixture was stirred for 1 h at 0° C., diluted with EtOAc (1000 mL) and washed with water (1000 mL) and brine (100 mL). The organic solution was then dried (MgSO$_4$) and the solvents were evaporated in vacuo. The residue was stirred with ether (100 mL). The product solidified and was collected by filtration to give 12.0 g (86% yield) of (6R)-trans-3-chloromethyl-7-[(2,5-dichlorophenyl)-thioacetamido]-8-oxo-5-thia-1-azabicyclo [4.2.0]oct-2-ene-2-carboxylate, diphenylmethyl ester, m.p. 120°°C. $^1$H NMR (300 MHz, CDCl$_3$) δ3.43 (d, J=18 Hz, 1H), 3.59 (d, J=18 Hz, 1H), 3.69 (d, J=17 Hz, 1H), 3.79 (d, J=17 Hz, 1H), 4.36 (d, J=12 Hz, 1H), 4.41 (d, J=12 Hz, 1H), 4.98 (d, J=5 Hz, 1H), 5.81 (dd, J=5, 9 Hz, 1H), 6.98 (s, 1H), 7.14–7.44 (m, 14H). Anal. Calcd for C$_{29}$H$_{23}$N$_2$O$_4$S$_2$Cl$_3$: C, 54.94; H, 3.66; N, 4.42. Found: C, 55.18; H, 3.84; N, 4.62.
Method b: (6R)-trans-3-Chloro methyl-7-amino-8-oxo-5-thia-1-azabicyclo[4.2.0]oct-2-ene-2-carboxylate, diphenyl-methyl ester, HCl salt (Otsuka, 248 g, 0.55 mol) was treated with NaHCO$_3$ (56 g, 0.66 mol) in water (1.6 L) at 0° C. The mixture was stirred at 0° C. for 0.5 h and then CH$_2$Cl$_2$ (1.5 L) was added. The biphasic mixture was filtered through Celite and the Celite pad was washed with CH$_2$Cl$_2$ (2 L total). The layers were separated and the organic solution was dried over anhydrous MgSO$_4$, filtered, and concentrated to a volume of ca. 2 L. The free amine solution was then added to a mixture of 2,5-dichlorothio-phenylacetic acid (130 g, 0.55 mol) and dicyclohexylcarbodiimide (144 g, 0.70 mol) in THF (1 L) at room temperature. The reaction mixture was stirred for 2.5 h and then was filtered through Celite, washing the Celite pad with several portions of acetone. The filtrate was concentrated in vacuo to give a solid mass. The solid was slurried in Et$_2$O and then collected by filtration, washing the solid with several portions of Et$_2$O.

The solid was dried under high vacuum over P$_2$O$_5$ to give 268 g (77% yield) of (6R)-trans-3-chloromethyl-7-[(2,5-dichlorophenyl)thioacetamido]-8-oxo-5-thia-1-azabicyclo [4.2.0]oct-2-ene-2-carboxylate, diphenylmethyl ester (see above for analytical data).

C. (6R)-trans-3-(4-Pyridylthiomethyl)-7-[(2,5-dichlorophenyl)-thioacetamido][-oxo-5-thia-1-azabicyclo [4.2.0]oct-2-ene-2-carboxylate, diphenylmethyl ester A solution of (6R)-trans-3-chloromethyl-7-[(2,5-dichlorophenyl)-thioacetamido]-8-oxo-5-thia-1-azabicyclo [4.2.0]oct-2-ene-2-carboxylate, diphenylmethyl ester (6.00 g, 9.46 mmol) in acetone (100 mL) was treated with sodium iodide (4.26 g, 28.4 mmol). The mixture was stirred at 20° C. for 3 h and then condensed under reduced pressure to a volume of 50 mL. The concentrated solution was diluted with EtOAc (200 mL) and washed with ice water (100 mL). The organic solution was washed with saturated NaHSO$_4$ (20 mL), dried (MgSO$_4$), and evaporated under reduced pressure. The residue was stirred with ether (30 mL). The product solidified and was collected by filtration to give 6.40 g of (6R)-trans-3-iodomethyl-7-[(2,5-dichlorophenyl)thio-acetamido]-8-oxo-5-thia-1-azabicyclo[4.2.0]oct-2-ene-2-carboxylate, diphenylmethyl ester (93% yield) as a tan solid, m.p. 124° C. $^1$H NMR (300 MHz, CDCl$_3$) δ3.43 (d, J=18 Hz, 1H), 3.69 (d, J=17 Hz, 1H), 3.70 (d, J=18 Hz, 1H), 3.78 (d, J=17 Hz, 1H), 4.27 (d, J=9 Hz, 1H), 4.33 (d, J=9 Hz, 1H), 4.96 (d, J=5 Hz, 1H), 5.75 (dd, J=5, 9 Hz, 1H), 7.00 (s, 1H), 7.20–7.46 (m, 14H). Anal. Calcd. for C$_{29}$H$_{23}$N$_2$O$_4$S$_2$Cl$_2$I: C, 48.01; H, 3.20; N, 3.86. Found: C, 48.00; H, 3.14; N, 3.76.

(6R)-trans-3-iodomethyl-7-[(2,5-dichlorophenyl) thioacetamido]-8-oxo-5-thia-1-azabicyclo[4.2.0]oct-2-ene-2-carboxylate, diphenylmethyl ester (300 g, 4.14 mmol) was dissolved in THF (50 mL) at 0° C. and treated with 4-mercaptopyridine (0.504 g, 4.54 mmol). A solution of 2,6-lutidine (0.576 g, 5.38 mmol) in THF (1 mL) was added next, and the reaction mixture was stirred at 0° C. for 0.5 h and then at 20° C. for 1 h. The mixture was diluted with ethyl acetate (500 mL) a nd the organic solution was washed with water (2×500 mL) and brine (100 mL). The solution was then dried (MgSO$_4$) and evaporated under reduced pressure to give an oil which was treated with Et$_2$O (50 mL) to give a solid. The solid was collected by filtration and purified by column chromatography on silica gel (CH$_2$Cl$_2$ to 30% EtOAc/CH$_2$Cl$_2$) to give 1.50 g of (6R)-trans-3-[(4-pyridylthiomethyl]-7-[(2,5-dichlorophenyl)-thioacetamido]-8-oxo-5-thia-1-azabicyclo[4.2.0]oct-2-ene-2-carboxylate, diphenylmethyl ester as a tan solid (49% yield), m.p. 122° C. $^1$H NMR (300 MHz, CDCl$_3$) δ3.37 (d, J=18 Hz, 1H), 3.52 (d, J=18 Hz, $^1$H), 3.68 (d, J=17 Hz, 1H), 3.76 (d, J=17 Hz, 1H), 3.96 (d, J=13 Hz, 1H), 4.16 (d, J=13 Hz, 1H), 4.93 (d, J=5 Hz, 1H), 5.76 (dd, J=5,9 Hz, 1H), 6.95–7.42 (m, 16H), 7.49 (d, J=9 Hz, 1H), 8.29 (d, J=6 Hz, 2H). Anal. Calcd. for C$_{34}$H$_{27}$N$_3$O$_4$S$_3$Cl$_2$: C, 57.62; H, 3.84; N, 5.93. Found: C, 57.27; H, 3.68; N, 5.79.

D. 1-[2-Carbooxy-2-propen-1-yl]-4-[[(6R)-trans-2-(diphenylmethyl-carboxy)-8-oxo-7-[(2,5-dichlorophenylthio)acetamido]-5-thia-1-azabicyclo[4.2.0]-oct-2-en-3-yl]methylthio]pyridinium bromide A solution of (6R)-trans-3-(4-pyridylthiomethyl)-7-[(2,5-dichlorophenyl)-thioacetamido]-8-oxo-5-thia-1-azabicyclo [4.2.0]oct-2-ene-2-carboxylate, diphenylmethyl ester (600 mg, 0.845 mmol) in 5 mL of DMF was treated with 2-(bromomethyl)acrylic acid (Aldrich) (279 mg, 1.69 mmol). This mixture was stirred at rt for 4 h, and then 50 mL of ether was added, resulting in the precipitation of the desired product. The solid was collected by filtration washing with ether to give 667 mg (85%) of 1-[2-carboxy-2- propen-1-yl]-4-[[(6R)-trans-2-(diphenylmethyl carboxy)-8-oxo-7-[(2,5-dichlorophenylthio)acetamido]-5-thia-1-azabicyclo [4.2.0]-oct-2-en-3-yl]methylthio]pyridinium bromide, as a tan solid. $^1$H NMR (DMSO-d$^6$) δ9.35 (d, J=8 Hz, 1H), 8.73 (d, J=7 Hz, 2H), 7.88 (d, J=7 Hz, 2H), 7.18–7.49 (m, 13H), 6.97 (s, 1H), 6.48 (s, 1H), 6.18 (s, 1H), 5.81 (dd, J=5,8 Hz, 1H), 5.35 (s, 2H), 5.23 (d, J=5 Hz, 1H), 4.31 (d, J=12 Hz, 1H), 7.23 (d, J=12 Hz, 1H), 3.95 (s, 2H), 3.83 (d, J=18 Hz, 1H), 3.59 (d, J=18 Hz, 1H). IR (KBr) 1780, 1714, 1626, 1450,1106 cm$^{-1}$; MS (ESI) 792 (MH)$^+$; Anal. calcd. for $C_{38}H_{31}N_3O_6S_3C_{12}$.HBr.0.35 HC(O)N(CH$_3$)$_2$.1.5 H$_2$O: C, 50.64; H, 4.08; N, 5.07. Found: C, 50.68, H, 3.93; N, 5.05.

E. 1-[2-Carboxy-2-propen-1-yl]-4-[[(6R)-trans-2-carboxy-8-oxo-7-(2,5-dichlorophenylthio)acetamido]-5-thia-1-azabicyclo]4.2.0]-oct-2-en-3-yl]methylthio]pyridinium bromide A slurry of 1-[2-carboxy-2-propen-1-yl]-4-[[(6R)-trans-2-(diphenylmethyl carboxy)-8-oxo-7-[(2,5-dichlorophenylthio)acetamido]-5-thia-1-azabicyclo[4.2.0]-oct-2-en-3-yl]methylthio]pyridinium bromide (580 mg, 0.665 mmol) in 22 mL of CH$_2$Cl$_2$ was cooled to 0° C. (ice bath) under an atmosphere of N$_2$. Anisole (2.8 mL) was added followed by trifluoroacetic acid (8 mL). The cooling bath was removed, and the reaction was allowed to stir at rt for 1 h. The solution was concentrated in vacuo to remove the CH$_2$Cl$_2$ and most of the trifluoroacetic acid. The residue was treated with ether to precipitate a yellow solid. This solid was collected by filtration washing with ether. The solid was stirred with ethyl acetate for 30 min. stirred with acetone for 30 min., collected by filtration, and dried in vacuo to give 322 mg (66%) of 1-[2-carboxy-2-propen-1-yl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium bromide as a tan solid. $^1$H NMR (DMSO-d6) δ9.27 (d, J=8 Hz, 1H), 8.73 (d, J=6 Hz, 2H), 8.06 (d, J=6 Hz, 2H), 7.45–8.48 (m, 2H), 7.24 (dd, J=2,9 Hz, 2H), 6.41 (s, 1H), 6.08 (s, 1H), 5.63 (dd, J=5,8 Hz, 1H), 5.19 (s, 2H), 5.09 (d, J=5 Hz, 1H), 4.43 (s, 2H), 3.92 (s, 2H), 3.70 (d, J=18 Hz, 1H), 3.48 (d, J=18 Hz, 1H). IR (KBr) 1774, 1702, 1680, 1628, 1106 cm$^{-1}$; MS (ESI) 626 (MH)+, Anal: Calcd for $C_{25}H_{21}N_3O_6S_3Cl_2$×HBr×0.5Me$_2$CO; C, 42.44; H, 3.13; N, 5.94. Found: C, 43.25; H, 3.42, N, 5.71.

Example 2

1[2-Carboxy-2-hydroxyethyl]-4-[[(6R)-trans-2-carboxy-8-oxo-7-(2,5-dichlorophenylthio)acetamido]-5-thia-1-azabicyclo[4.2.0]-oct-2-en-3-yl]methylthio]pyridinium chloride A. (6R)-trans-3-Chloromethyl-7-[(2,5-dichlorophenyl)-thioacetamido]-8-oxo-5-thia-1-azabicyclo[4.2.0]oct-2-ene-2-carboxylic acid A slurry of (6R)-trans-3-chloromethyl-7-[(2,5-dichlorophenyl)--thioacetamido]-8-oxo-5-thia-1-azabicyclo[4.2.0]oct-2-ene-2-carboxylate, diphenylmethyl ester (10.0 g, 15.8 mmol) in CH$_2$Cl$_2$ (200 mL) at 0° C. was treated with anisole (24 mL) and then trifluoroacetic acid (80 mL). The solution was stirred for 1 h at 0° C. and then concentrated under reduced pressure. The residue was stirred with Et$_2$O, and the resulting solid was collected by filtration to give 5.20 g of (6R)-trans-3-chloro-methyl-7-[(2,5-dichlorophenyl)-thioacetamido]-8-oxo-5-thia-1-azabicyclo[4.2.0]oct-2-ene-2-carboxylic acid as a white solid (70% yield), m.p. 125° C. $^1$H NMR (300 MHz, DMSO-d$_6$) δ9.28 (d, J=8 Hz, 1H), 7.47 (dd, J=2, 8 Hz, 2H), 7.24 (dd, J=2, 8 Hz, 1H), 5.70 (dd, J=5, 8 Hz, 1H), 5.13 (d, J=5 Hz, 1H), 4.58 (d, J=11 Hz, 1H), 4.52 (d, J=11 Hz, 1H), 3.91 (s, 2H), 3.70 (d, J=18 Hz, 1H) 3.51 (d, J=18 Hz, 1H).

B. 1-[2-carboxy-2-hydroxyethyl]-4-[(6R)-trans-2-carboxy-8-oxo-7-[(2,5-dichlorophenylthio)acetamido]-5-thia-1-azabicyclo[4.2.0]-oct-2-en-3-yl]methylthio]pyridinium chloride 1. Preparation of 1-[N-(2-carboxy-2-hydroxyethyl)-4-thiopyridone odium salt A solution of D,L-isoserine (1.00 g, 9.52 mmol) in a mixture of water (10 mL) and ethanol (10 mL) was treated with 9.52 mL of 1N NaHCO$_3$ followed by thiopyrone (1.07 g, 9.52 mmol). The mixture was stirred at reflux for 2 h, and concentrated in vacuo. The residue was triturated with ether to give 1.78 g (85%) of 1-[N-(2-carboxy-2-hydroxyethyl)-4-thiopyridone sodium salt as a brown solid. $^1$H NMR (DMSO-d$^6$) δ7.50 (d, J=7 Hz, 2H), 7.08 (d, J=7 Hz, 2H), 4.17 (dd, J=3,4 Hz, 1H), 4.03 (dd, J=6,14 Hz, 1H), 3.83 (dd, J=3,6 Hz, 1H). $^{13}$C (75 MHz) δ188.62, 172.79, 137.09, 129.44, 70.78, 60.40; IR (KBr) 3384 (br), 1622, 1114 cm$^{-1}$; MS (ESI) 198 (M)$^-$.

2. 1-[2-Carboxy-2-hydroxyethyl]-4-[[(6R)-trans-2-carboxy-8-oxo-7-[(2,5-dichlorophenylthio)acetamido]-5-thia-1-azabicyclo[4.2.0]-oct-2-en-3-yl]methylthio]pyridinium chloride A solution of cephem 6(R)-trans-3-chloromethyl-7-[(2,5-dichlorophenyl)-thioacetamido]-8-oxo-5-thia-1-azabicyclo[4.2.0]oct-2-ene-2-carboxylic acid (60 0 mg, 1.28 mmol) in 5 mL of DMF was treated with thiopyridone 1-[N-(2-carboxy-2-hydroxyethyl)-4-thiopyridone Na salt(255 mg, 1.28 mmol). After stirring the mixture for 3 h at rt under a nitrogen atmosphere, it was concentrated in vacuo. The residue was stirred with ether until a solid formed. This solid was collected by filtration and washed with ethyl acetate

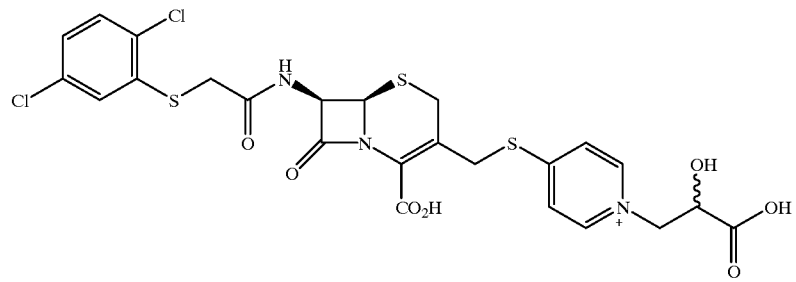

followed by acetone to give 564 mg (63%) of 1-[2-carboxy-2-hydroxyethyl]-4-[[(6R)-trans-2-carboxy-8-oxo-7-1(2,5-dichlorophenylthio)acetamido]-5-thia-1-azabicyclo[4.2.0]-oct-2-en-3-yl]methylthio]pyridinium chloride as a tan solid. $^1$H NMR (DMSO-d$^6$) δ9.36 (d, J=6 Hz, 1H), 8.67 (d, J=6 Hz, 2H), 8.07 (d, J=6 Hz, 2H), 7.42–7.48 (m, 2H), 7.21 (dd, J=2,9 Hz 1H), 5.57 (dd, J=5,8 Hz, 1H), 5.05 (d, J=5 Hz, 1H), 4.80 (d, J=11 Hz, 1H), 4.39–4.60 (m, 4H), 3.93 (s, 2H), 3.64 (d, J=18 Hz, 1H), 3.45 (d, J=18 Hz, 1H). IR (KBr) 3422 (br), 1774, 1703, 1675, 1628, 1450, 1108 cm$^{-1}$. MS (ESI) 630 (MH)$^+$; Anal. Calcd. for $C_{24}H_{21}O_7N_3S_3Cl_2$. HCl.2.0 H$_2$O: C, 40.97; H, 3.69; N, 5.97. Found: C, 40.95; H, 3.43; N, 5.83

The following additional compounds were prepared according to the general procedures of Examples 1 and 2 by varying the thiol starting material and the pyridine or thiopyridone derivative:

| Example No. | Ar | R$^1$ | R$^2$ | R$^3$ | Isolated As |
|---|---|---|---|---|---|
| 1 | 2,5-diClPh | CH$_2$=C(CO$_2$H)CH$_2$– | H | H | HBr salt |
| 2 | 2,5-diClPh | (±)-CH$_2$CH(OH)CO$_2$H | H | H | HCl salt |
| 3 | 2,5-diClPh | CH$_2$CO$_2$H | H | H | HBr Salt |
| 4 | 2,5-diClPh | (CH$_2$)$_3$CO$_2$H | H | H | zwitterion |
| 5 | 2,5-diClPh | (CH$_2$)$_5$CO$_2$H | H | H | zwitterion |
| 6 | 2,5-diClPh | (R)- CH$_2$=C(CO$_2$H)CH$_2$– | H | H | HCl salt |
| 7 | 2,5-diClPh | 1-(CO$_2$H)cyclopropyl-CH$_2$– | H | H | zwitterion |
| 8 | 2,5-diClPh | (L)- –CH$_2$CH(CO$_2$H)CH$_2$OH | H | H | HCl salt |
| 9 | 2,5-diClPh | (polyhydroxy sugar derivative) | H | H | zwitterion |
| 10 | 2,5-diClPh | (L)- –CH$_2$CH(CO$_2$H)CH$_2$CH$_2$SCH$_3$ | H | H | HCl salt |

-continued

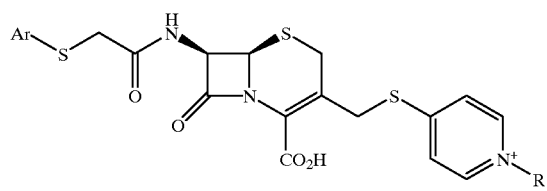

| Example No. | Ar | R¹ | R² | R³ | Isolated As |
|---|---|---|---|---|---|
| 11 | 2,5-diClPh | (L)- [structure: CH(CO$_2$H)CH$_2$CH$_2$S(O)CH$_3$] | H | H | zwitterion |
| 12 | 2,5-diClPh | (L)- [structure: CH(CO$_2$H)CH$_2$CH$_2$SO$_2$CH$_3$] | H | H | zwitterion |
| 13 | 2,5-diClPh | (L)- [structure: CH(CO$_2$H)CH$_2$CH$_2$SO$_2$NH$_2$] | H | H | HCl salt |
| 14 | 2,5-diClPh | (L)- [structure: CH(CO$_2$H)CH$_2$CH$_2$CH$_2$NHC(O)NH$_2$] | H | H | HCl salt |
| 15 | 2,5-diClPh | [structure: CH(CO$_2$H)-(4-hydroxyphenyl)] | H | H | HCl salt |
| 16 | 2,5-diClPh | [structure: CH(CO$_2$H)CH$_2$-(2-thienyl)] | H | H | HCl salt |
| 17 | 2,5-diClPh | CH$_2$CH(OH)CH$_2$CO$_2$H | H | H | zwitterion |
| 18 | 2,5-diClPh | (S)-CH$_2$CH$_2$CH$_2$CH$_2$CH$_2$CH(OH)CO$_2$H | H | H | HCl salt |
| 19 | 3,5-diClPyr | " | H | H | HCl salt |
| 20 | 2,5-diClPh | (S)-CH$_2$CH$_2$CH$_2$CH(OH)CO$_2$H | H | H | zwitterion |
| 21 | 3,5-diClPyr | " | H | H | zwitterion |
| 22 | 2,5-diClPh | (R)-CH$_2$CH$_2$CH$_2$CH(OH)CO$_2$H | H | H | HCl salt |
| 23 | 3,5-diClPyr | " | H | H | HCl salt |
| 24 | 2,5-diClPh | (S)-CH$_2$CH$_2$CH(OH)CO$_2$H | H | H | HCl salt |
| 25 | 3,5-diClPyr | " | H | H | HCl salt |
| 26 | 3,5-diClPyr | (±)-CH$_2$CH(OH)CO$_2$H | H | H | HCl salt |
| 27 | 2,5-diClPh | [structure: CH$_2$C(CH$_3$)$_2$CH(OH)CO$_2$H] | H | H | HCl salt |

-continued

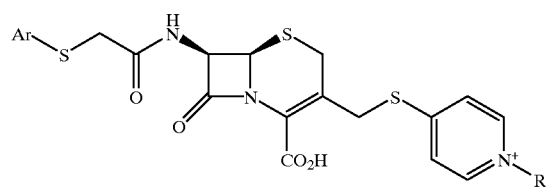

| Example No. | Ar | R¹ | R² | R³ | Isolated As |
|---|---|---|---|---|---|
| 28 | 2,5-diClPh | (dihydroxy-CO₂H sidechain, R,R) | H | H | TFA salt |
| 29 | 2,5-diClPh | (dioxolane-CO₂H, R,R, dimethyl) | H | H | HCl salt |
| 30 | 2,5-diClPh | (CH₂-CH(=O)-... CO₂H sidechain) | H | H | zwitterion |
| 31 | 3,5-diClPyr | " | H | H | zwitterion |
| 32 | 2,5-diClPh | (CH₂-C(=O)-CH₂-CO₂Me) | H | H | HCl salt |
| 33 | 2,5-diClPh | (CH₂-C(=O)-CH₂CH₂-CO₂H) | H | H | zwitterion |
| 34 | 2,5-diClPh | (CH₂-C(CH₃)₂-CO₂H with ketone) | H | H | HCl salt |
| 35 | 2,5-diClPh | CH₂CHFCO₂H | H | H | HCl salt |
| 36 | 2,5-diClPh | CH₂CH₂CHFCO₂H | H | H | HCl salt |
| 37 | 2,5-diClPh | CH₂CH₂CF₂CO₂H | H | H | HCl salt |
| 38 | 2,5-diClPh | CH₂CH₂SCH₂CO₂H | H | H | HCl salt |
| 39 | 2,5-diClPh | CH₂CH₂CH₂SCH₂CH₂CO₂H | H | H | HCl salt |
| 40 | 2,5-diClPh | CH₂C(O)NHCH₂CO₂H | H | H | HBr salt |
| 41 | 2,4,5-triClPh | " | H | H | HBr salt |
| 42 | 3,5-diClPyr | " | H | H | HBr salt |
| 43 | 2,5-diClPh | CH₂C(O)NHCH₂CH₂CO₂H | H | H | HBr salt |
| 44 | 3,5-diClPyr | " | H | H | HBr salt |
| 45 | 2,5-diClPh | (±)-CH₂C(O)NHCH₂CH(OH)CO₂H | H | H | HCl salt |
| 46 | 2,5-diClPh | (L)- (CH₂C(O)NH-Ser-CO₂H) | H | H | HBr salt |
| 47 | 3,5-diClPyr | " | H | H | HBr salt |

-continued

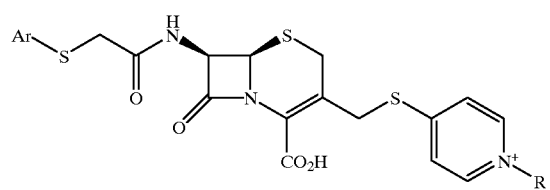

| Example No. | Ar | R¹ | R² | R³ | Isolated As |
|---|---|---|---|---|---|
| 48 | 2,5-diClPh | (L)- [CH₂C(O)NH-CH(CO₂H)-CH₂CH₂SMe] | H | H | HCl salt |
| 49 | 2,5-diClPh | (L)- [CH₂C(O)-N(pyrrolidine-CO₂H)] | H | H | HCl salt |
| 50 | 2,5-diClPh | (L)- [CH₂C(O)NH-CH(CO₂H)-CH₂Ph] | H | H | HCl salt |
| 51 | 2,5-diClPh | [CH₂C(O)NH-CH(CO₂H)-CH₂-C₆H₄-4-OH] | H | H | HCl salt |
| 52 | 2,5-diClPh | [CH₂C(O)NH-CH(CO₂H)-CH₂-imidazolyl] | H | H | zwitterion |
| 53 | 2,5-diClPh | [CH(CH₃)C(O)NH-CH₂CO₂H] | H | H | HCl salt |
| 54 | 2,5-diClPh | [CH₂C(O)-N(CH₃)-CH₂CO₂H] | H | H | HCl salt |
| 55 | 2,5-diClPh | CH₂SO₃⁻ | H | H | zwitterion |
| 56 | 2,5-diClPh | CH₂CH₂SO₃⁻ | H | H | zwitterion |
| 57 | 2,5-diClPh | " | 2-Me | 6-Me | HCl salt |
| 58 | 2,5-diClPh | " | H | 2-Et | HCl salt |
| 59 | 2,5-diClPh | " | 2-Me | 3-Me | HCl salt |
| 60 | 2,5-diClPh | CH₂CONHCH₂CH₂SO₃⁻ | H | H | HBr salt |
| 61 | 3,5-diClPyr | " | H | H | zwitterion |
| 62 | 2,5-diClPh | (CH₂)₂CONHCH₂CH₂SO₃⁻ | H | H | zwitterion |
| 63 | 3,5-diClPyr | " | H | H | HCl salt |
| 64 | 2,5-diClPh | [(CH₂)₃-S-(1H-tetrazol-5-yl)] | H | H | HCl salt |

-continued
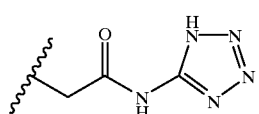
| Example No. | Ar | R¹ | R² | R³ | Isolated As |
|---|---|---|---|---|---|
| 65 | 2,5-diClPh | 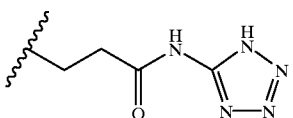 | H | H | HCl salt |
| 66 | 2,5-diClPh | 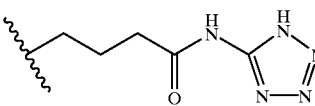 | H | H | HCl salt |
| 67 | 2,5-diClPh | 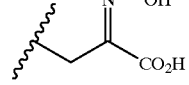 | H | H | HCl salt |
| 68 | 2,5-diClPh | 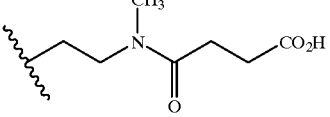 | H | H | HBr salt |
| 69 | 2,5-diClPh | 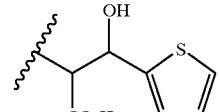 | H | H | zwitterion |
| 70 | 2,5-diClPh | 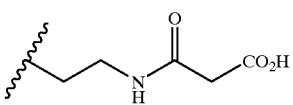 | H | H | HCl salt |
| 71 | 2,5-diClPh |  | H | H | HCl salt |
| 72 | 2,5-diClPh | $CH_2CH_2SCH_2CH_2SO_3-$ | H | H | HCl salt |

TABLE

NMR DATA

| Cmpd of Ex No | H-2 | H-6 | H-7 | H-3' | H-7' | NH | ArH | S-PyrH | R | MS Data |
|---|---|---|---|---|---|---|---|---|---|---|
| 1 | 3.70(d, J=18) 3.48(d, J=18) | 5.09(d, J=5) | 5.63(dd, J=5,8) | 4.43(s) | 3.92(s) | 9.27(d, J=8) | 7.45–7.48(m) 7.24(dd, J=2,9) | 8.73(d, J=6) 8.06(d, J=6) | 6.41(s) 6.08(s) 5.19(s) | $MH^+ = 626$ |
| 2 | 3.64(d, J=18) 3.45(d, J=18) | 5.05(d, J=5) | 5.57(dd, J=5,8) | 4.80(d, J=11) 4.39–4.60(m) | 3.93(s) | 9.36(d, J=6) | 7.42–7.48(m) 7.21(dd, J=2,9) | 8.67(d, J=6) 8.07(d, J=6) | 4.39–4.60(m) | $MH^+ = 630$ |
| 3 | 3.69(d, J=17) 3.49(d, J=18) | 5.10(d, J=4) | 5.63(dd, J=4,8) | 4.47(d, J=13) 4.34(d, J=13) | 3.91(s) | 9.28(d, J=8) | 7.44–7.48(m) 7.23(dd, J=2,9) | 8.58(d, J=6) 8.04(d, J=6) | 4.96(br s) | $MH^+ = 600$ |
| 4 | 3.46(d, J=17) 3.30(d, J=17) | 4.93(d, J=5) | 5.42(dd, J=5,8) | 4.62(d, J=14) 4.37(d, J=14) | 3.97(d, J=15) 3.89(d, J=15) | 9.53(d, J=8) | 7.49–7.52(m) 7.20(d, J=2,8) | 8.71(d, J=7) 8.26(d, J=7) | 4.38–4.50(m) 1.80–2.05(m) | $M^+ = 650$ |
| 5 | 3.32(d, J=17) 2nd under water peak | 4.93(d, J=5) | 5.43(dd, J=5,8) | 4.57(d, J=14) 4.47(d, J=14) | 3.96(d, J=15) 3.89(d, J=15) | 9.55(d, J=8) | 7.47–7.49(m) 7.22(d, J=2,8) | 8.77(d, J=7) 8.27(d, J=7) | 4.40–4.45(m) 1.90–1.95(m) 1.72–1.85(m) 1.38–1.55(m) 1.07–1.25(m) | $MH^+ = 653$ |
| 6 | 3.58(d, J=18) 3.41(d, J=18) | 5.01(d, J=5) | 5.55(dd, J=5,8) | 4.68(d, J=14) 4.30(d, J=14) | 4.00–3.90(m) | 9.37(d, J=8) | 7.51(d, J=2) 7.46(d, J=8) 7.23(dd, J=2,8) | 8.62(d, J=7) 8.16(d, J=7) | 4.93–5.00(m) 1.70(d, J=7) | $MH^+ = 614$ |
| 7 | 3.49(d, J=18) 3.38(d, J=18) | 4.99(d, J=5) | 5.48(dd, J=5,8) | 4.77(d, J=14) 4.26(d, J=14) | 3.92(s) | 9.34(d, J=8) | 7.48(d, J=2) 7.46(d, J=8) 7.24(dd, J=8,2) | 8.58(d, J=7) 8.32(d, J=7) | 1.48(br s) 1.37(br s) | $MH^+ = 625$ |
| 8 | 3.76(d, J=18) 3.34–3.40(m) | 5.13(d, J=5) | 5.68(dd, J=5,8) | 4.43(d, J=15) 4.36(d, J=15) | 3.91(s) | 9.31(d, J=8) | 7.44–7.47(m) 7.21(d, J=2,8) | 8.77(d, J=7) 8.04(d, J=7) | 4.21–4.23(m) 4.06–4.09(m) | $MH^+ = 632$ |
| 9 | 3.34–3.54(m) | 5.09(d, J=5) | 5.62(dd, J=5,8) | 4.41(s) | 3.91(s) | 9.31(d, J=8) | 7.43–7.47(m) 7.22(dd, J=2,9) | 8.69(d, J=7) 7.92(d, J=7) | 3.34–3.54(m) 46.2(s) 3.31(br s) | $MH^+ = 720$ |
| 10 | 3.71(d, J=18) 3.51(d, J=18) | 5.11(d, J=5) | 5.64(dd, J=5,8) | 4.46(d, J=13) 4.37(d, J=13) | 3.91(s) | 9.29(d, J=8) | 7.44–7.48(m) 7.23(dd, J=2,8) | 8.74(d, J=7) 8.00(d, J=7) | 5.18–5.23(br s) 2.38–2.50(br s) 2.00(s) | $M^+ = 673$ |

TABLE-continued

NMR DATA

| Cmpd of Ex No | H-2 | H-6 | H-7 | H-3' | H-7' | NH | ArH | S-PyrH | R | MS Data |
|---|---|---|---|---|---|---|---|---|---|---|
| 11 | 3.70(d, J=18)<br>3.50(d, J=18) | 5.11(d, J=5) | 5.64(dd, J=5,8) | 4.49(d, J=13)<br>4.33(d, J=13) | 3.91(s) | 9.28(d, J=8) | 7.48(d, J=2)<br>7.46(d, J=8)<br>7.23(dd, J=2,8) | 8.70(d, J=7)<br>8.01(d, J=7) | 4.96–5.05(m)<br>2.60–2.74(m)<br>2.49(s)<br>2.39–2.53(m) | MH⁻ = 688 |
| 12 | 3.71(d, J=18)<br>3.50(d, J=18) | 5.11(d, J=5) | 5.65(dd, J=5,8) | 4.47(d, J=13)<br>4.33(d, J=13) | 3.91(s) | 9.28(d, J=8) | 7.47(d, J=2)<br>7.46(d, J=8)<br>7.23(dd, J=2,8) | 8.66(d, J=7)<br>7.99(d, J=7) | 4.93–5.00(m)<br>2.98–3.12(m)<br>2.94(s)<br>2.64–2.80(m) | MH⁺ = 690 |
| 13 | 3.73(d, J=18)<br>3.53(d, J=18) | 5.13(d, J=5) | 5.66(dd, J=5,8) | 4.47(d, J=13)<br>4.37(d, J=13) | 3.93(s) | 9.30(d, J=8) | 7.46–7.49(m)<br>7.25(dd, J=2,8) | 8.68(d, J=7)<br>8.00(d, J=7) | 6.89(s)<br>5.02–5.10(m)<br>3.12–3.25(m)<br>2.72–2.98(m) | M⁺ = 706 |
| 14 | 3.69(d, J=18)<br>3.53(d, J=18) | 5.10(d, J=5) | 5.63(dd, J=5,8) | 4.47(d, J=13)<br>4.38(d, J=13) | 3.91(s) | 9.27(d, J=8) | 7.44–7.48(m)<br>7.23(dd, J=2,8) | 8.71(d, J=7)<br>8.00(d, J=7) | 6.10–6.20(m)<br>5.35–5.60(m)<br>5.00–5.11(m)<br>2.20–2.40(m)<br>1.22–1.40(m)<br>1.00–1.20(m) | M⁺ = 699 |
| 15 | 3.56(d, J=18)<br>3.48(d, J=18) | 5.50(d, J=5) | 5.57(dd, J=5,8) | 4.51(d, J=13)<br>4.32(d, J=13) | 3.97(d, J=8) | 9.38(d, J=8) | 7.46–7.52(m)<br>7.20–7.31(m) | 8.56(d, J=7)<br>8.06(d, J=7) | 7.22(d, J=7)<br>6.78(d, J=7)<br>6.15(s) | MH⁺ = 694 |
| 16 | 3.67(d, J=18)<br>3.43(d, J=18) | 5.06(d, J=5) | 5.61(dd, J=5,8) | 4.37(d, J=13)<br>4.26(d, J=13) | 3.96(s) | 9.27(d, J=8) | 7.42–7.45(m)<br>7.21(dd, J=2,8) | 8.60(d, J=7)<br>7.87(d, J=7) | 7.26(d, J=5)<br>6.77–6.85(m)<br>5.37–5.42(m)<br>3.74–3.85(m) | M⁺ = 695 |
| 17 | 3.49(d, J=17)<br>3.34(d, J=17) | 4.94(d, J=5) | 5.44(dd, J=5,8) | 4.62(d, J=12)<br>4.52(d, J=12) | 3.98(d, J=15)<br>3.96(d, J=12) | 9.38–9.42(m) | 8.20(dd, J=2,8)<br>7.40–7.49(m) | 8.63(d, J=6)<br>8.25(d, J=6) | 4.20–4.40(m)<br>2.98(s)<br>1.80–2.20(m) | M⁺ = 644 |
| 18 | 3.52(d, J=18)<br>3.33(d, J=18) | 4.92(d, J=5) | 5.46(dd, J=5,8) | 4.54(d, J=13)<br>4.43(d, J=13) | 3.89(s) | 9.22(d, J=8) | 7.43–7.48(m)<br>7.20–7.24(m) | 8.70(d, J=7)<br>8.17(d, J=7) | 4.36–4.46(m)<br>2.84–3.92(m) | M⁺ = 672 |

TABLE-continued

NMR DATA

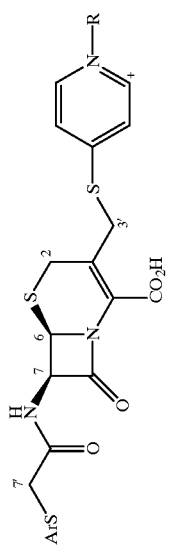

| Cmpd of Ex No | H-2 | H-6 | H-7 | H-3' | H-7' | NH | ArH | S-PyrH | R | MS Data |
|---|---|---|---|---|---|---|---|---|---|---|
| 19 | 3.53(d, J=18) 3.33(d, J=18) | 4.92(d, J=5) | 5.47(dd, J=5,8) | 4.53(d, J=13) 4.42(d, J=13) | 3.98(s) | 9.23(d, J=8) | 7.50(s) | 8.70(d, J=7) 8.16(d, J=7) | 1.75–1.85(m) 1.54–1.63(m) 1.15–1.40(m) | |
| 20 | 3.51(d, J=18) 3.39(d, J=18) | 4.96(d, J=5) | 5.48(dd, J=5,8) | 4.49(d, J=13) 4.41(d, J=13) | 3.91(s) | 9.28(d, J=8) | 7.43–7.47(m) 7.21–7.24(m) | 8.70(d, J=7) 8.20(d, J=7) | 4.35–4.45(m) 3.85–3.94(m) 1.77–1.88(m) 1.49–1.59(m) 1.10–1.40(m) | M$^+$ = 673 |
| 21 | 3.74(d, J=18) 3.49(d, J=18) | 5.13(d, J=5) | 5.68(dd, J=5,8) | 4.37(d, J=13) 4.35(d, J=13) | 4.00(s) | 9.29(d, J=8) | 7.50(s) | 8.77(d, J=7) 8.00(d, J=7) | 4.36–4.44(m) 3.85–3.95(m) 1.85–1.95(m) 1.40–1.70(m) | M$^+$ = 658 |
| 22 | 3.53(d, J=18) 3.36(d, J=18) | 4.96(d, J=5) | 5.49(dd, J=5,8) | 4.49(d, J=13) 4.42(d, J=13) | 3.99(s) | 9.31(d, J=8) | 7.43–7.48(m) 7.20–7.24(m) | 8.72(d, J=7) 8.21(d, J=7) | 4.42–4.47(m) 3.90–4.00(m) 1.90–1.99(m) 1.45–1.70(m) | M$^+$ = 659 |
| 23 | 3.55(d, J=18) 3.35(d, J=18) | 4.97(d, J=5) | 5.49(dd, J=5,8) | 4.49(d, J=13) 4.42(d, J=13) | 3.99(s) | 9.31(d, J=8) | 7.51(s) | 8.73(d, J=7) 8.20(d, J=7) | 4.40–4.45(m) 3.90–4.01(m) 1.80–1.97(m) 1.40–1.65(m) | M$^+$ = 658 |
| 24 | 3.47(d, J=18) 3.30(d, J=18) | 4.93(d, J=5) | 5.42(dd, J=5,8) | 4.60(d, J=13) 4.33(d, J=13) | 3.92(s) | 9.28(d, J=8) | 7.43–7.49(m) 7.20–7.24(m) | 8.66(d, J=7) 8.26(d, J=7) | 4.40–4.46(m) 3.90–4.02(m) 1.88–1.97(m) 1.40–1.65(m) | M$^+$ = 658 |
| 25 | 3.73(d, J=18) 3.48(d, J=18) | 5.14(d, J=5) | 5.68(dd, J=5,8) | 4.40(d, J=13) 4.34(d, J=13) | 4.01(s) | 9.35(d, J=8) | 7.52(s) | 8.75(d, J=7) 7.98(d, J=7) | 4.44–4.48(m) 3.92–4.02(m) 1.99–2.17(m) | M$^+$ = 644 |
| | | | | | | | | | 4.50–4.50(m) 3.90–4.10(m) 2.07–2.28(m) | M$^+$ = 645 |

TABLE-continued

NMR DATA

| Cmpd of Ex No | H-2 | H-6 | H-7 | H-3' | H-7' | NH | ArH | S-PyrH | R | MS Data |
|---|---|---|---|---|---|---|---|---|---|---|
| 26 | 3.62(d, J=18) 3.40(d, J=18) | 4.99(d, J=4) | 5.53(dd, J=5,7) | 4.68(d, J=11) 4.22–4.50(m) | 4.00(s) | 9.37(d, J=8) | 7.41(s) | 8.48(d, J=6) 7.93(d, J=6) | 4.22–4.50(m) | MH+ = 631 |
| 27 | 3.49(d, J=18) 3.68–3.74(m) (Overlaps with R) | 5.09(d, J=5) | 5.63(dd, J=5,8) | 4.52(d, J=13) Overlaps with R | 3.93(s) | 9.35(d, J=8) | 7.43–7.46(m) 7.21–7.24(m) | 8.72(d, J=6) 8.02(d, J=6) | 4.41(s) overlaps with H-3' 3.70(s) Overlaps w/H-2 0.92(s) | MH+ = 672 |
| 28 | 3.68(d, J=18) 3.45(d, J=18) | 5.09(d, J=5) | 5.63(dd, J=5,8) | 4.61(d, J=13) 4.41(d, J=13) | 3.92(s) | 9.26(d, J=8) | 7.46–7.48(m) 7.23–7.26(m) | 8.62(d, J=7) 8.06(d, J=7) | 4.30–4.40(m) 3.90–4.10(m) 3.70–3.90(m) | M+ = 661 |
| 29 | 3.61(d, J=18) 3.37(d, J=18) | 5.01(d, J=5) | 5.54(dd, J=5,8) | 4.48(d, J=13) 4.37(d, J=13) | 3.90(s) | 9.27(d, J=8) | 7.43–7.46(m) 7.20–7.24(m) | 8.68(d, J=7) 8.10(d, J=7) | 4.70–4.80(m) 4.35–4.50(m) 3.40–3.80(m) 1.47(s) 1.23(s) | M+ = 760 |
| 30 | 3.51(d, J=17) 3.35(d, J=17) | 4.97(d, J=5) | 5.46(dd, J=5,8) | 4.74(d, J=14) 4.30(d, J=14) | 3.91(s) | 9.20(d, J=8) | 7.45–7.50(m) 7.24(dd, J=9,2) | 8.48(d, J=7) 8.38(d, J=7) | 5.75(s) | M+ = 627 |
| 31 | 3.53(d, J=17) 3.39(d, J=17) | 4.99(d, J=5) | 5.46(dd, J=5,8) | 4.76(d, J=14) 4.31(d, J=14) | 4.03(d, J=16) 3.96(d, J=16) | 9.25(d, J=8) | 7.54(s) | 8.49(d, J=7) 8.39(d, J=7) | 5.76(s) | M+ = 628 |
| 32 | 3.68(d, J=18) 3.50(d, J=18) | 5.11(d, J=5) | 5.66(m) | 4.40(br s) | 3.91(s) | 9.30(d, J=8) | 7.46(m) 7.22(m) | 8.55(d, J=7) 7.67(d, J=7) | 3.88(s) 2.87(s) 2.70(s) | MH+ = 655 |
| 33 | 3.57(d, J=19) The 2nd H-2 proton is obscured by the water peak | 5.00(d, J=5) | 5.55(m) Overlaps with R | 4.59(d, J=14) 4.36(d, J=13) | 3.89(s) | 9.19(d, J=8) | 7.44–7.47(m) 7.23(dd, J=2,9) | 8.43(d, J=5) 8.31(d, J=5) | 5.56(s) Overlaps with H-7 2.95(t, J=7) 2.65(t, J=7) | MH+ = 656 |

TABLE-continued

NMR DATA

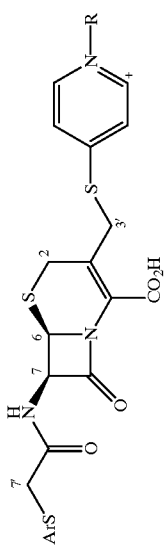

| Cmpd of Ex No | H-2 | H-6 | H-7 | H-3' | H-7' | NH | ArH | S-PyrH | R | MS Data |
|---|---|---|---|---|---|---|---|---|---|---|
| 34 | 3.75(d, J=18) 3.53(d, J=18) | 5.13(d, J=5) | 5.67(dd, J=5,8) | 4.40(s) | 3.96(s) | 9.40(d, J=8) | 7.45–7.49(m) 7.24(dd, J=2,9) | 8.91(d, J=6) 8.03(d, J=6) | 4.76(s) 1.12(s) | MH− = 668 |
| 35 | 3.60(d, J=18) 3.41(d, J=18) | 5.02(d, J=5) | 5.54(dd, J=5,8) | 4.54(d, J=13) 4.41(d, J=13) | 3.92(s) | 9.37(d, J=9) | 7.43–7.48(m) 7.21(dd, J=2,9) | 8.63(d, J=6) 8.13(d, J=5) | 5.18(br s) 4.80–5.00(m) | MH+ = 632 |
| 36 | 3.44(d, J=18) | 5.05(d, J=4) | 5.59(dd, J=5,7) | 4.36–4.38(m) | 3.90(s) | 9.33(d, J=8) | 7.43–7.46(m) 7.22(d, J=7) | 8.77(d, J=6) 8.03(d, J=6) | 5.08–5.14(m) 4.93–4.99(m) 4.62(br s) 2.35–2.51(m) | MH− = 646 |
| 37 | 3.70(d, J=18) 3.48(d, J=18) | 5.09(d, J=5) | 5.62(dd, J=5,8) | 4.40(s) | 3.92(s) | 9.35(d, J=8) | 7.43–7.46(m) 7.22(dd, J=2,8) | 8.83(d, J=6) 8.02(d, J=6) | 4.63(br s) 2.48–2.69(m) | MH+ = 664 |
| 38 | 3.76(d, J=18) 3.52(d, J=18) | 5.15(d, J=5) | 5.70(dd, J=5,8) | 4.40(br s) | 3.93(s) | 9.31(d, J=8) | 7.46–7.49(m) 7.25(dd, J=2,8) | 8.80(d, J=7) 8.06(d, J=7) | 4.66(t, J=6) 3.46(s) 3.15(t, J=6) | M+ = 659 |
| 39 | 3.77(d, J=18) 3.52(d, J=18) | 5.16(d, J=5) | 5.72(dd, J=5,8) | 4.40(br s) | 3.94(s) | 9.31(d, J=8) | 7.48–7.50(m) 7.26(dd, J=2,8) | 8.80(d, J=7) 8.03(d, J=7) | 4.50(t, J=6) 3.22–3.45(m) 2.68–2.74(m) 2.51–2.57(m) 2.15(t, J=7) | M+ = 687 |
| 40 | 3.74(d, J=18) 3.50(d, J=18) | 5.13(d, J=5) | 5.68(dd, J=5,8) | 4.42(d, J=13) 4.35(d, J=13) | 3.90(s) | 9.26(d, J=8) | 7.44–7.47(m) 7.21–7.25(m) | 8.63(d, J=7) 8.01(d, J=7) | 8.92(t, J=6) 5.30(s) 3.86(d, J=6) | M+ = 657 |
| 41 | 3.75(d, J=18) 3.51(d, J=18) | 5.13(d, J=5) | 5.68(dd, J=5,8) | 4.39(d, J=13) 4.37(d, J=13) | 3.92(s) | 9.26(d, J=8) | 7.84(s) 7.65(s) | 8.63(d, J=7) 8.01(d, J=7) | 8.91(t, J=6) 5.30(s) 3.86(d, J=6) | M+ = 691 |
| 42 | 3.74(d, J=18) 3.51(d, J=18) | 5.13(d, J=5) | 5.67(dd, J=5,8) | 4.43(d, J=13) 4.35(d, J=13) | 3.99(s) | 9.28(d, J=8) | 7.50(s) | 8.64(d, J=7) 8.01(d, J=7) | 8.92(t, J=7) 5.31(s) 3.86(d, J=7) | M+ = 658 |
| 43 | 3.72(d, J=18) 3.49(d, J=18) | 5.11(d, J=5) | 5.67(dd, J=5,8) | 4.45(d, J=13) 4.35(d, J=13) | 3.90(s) | 9.24(d, J=8) | 7.44–7.47(m) 7.21–7.25(m) | 8.61(d, J=7) 8.05(d, J=7) | 8.61(s) overlaps w/pyr H | M+ = 671 |

TABLE-continued

NMR DATA

| Cmpd of Ex No | H-2 | H-6 | H-7 | H-3' | H-7' | NH | ArH | S-PyrH | R | MS Data |
|---|---|---|---|---|---|---|---|---|---|---|
| 44 | 3.75(d, J=18)<br>3.51(d, J=18) | 5.14(d, J=5) | 5.68(dd, J=5,8) | 4.42(d, J=13)<br>4.35(d, J=13) | 3.99(s) | 9.28(d, J=8) | 7.50(s) | 8.62(d, J=7)<br>8.01(d, J=7) | 5.19(s)<br>3.30(t, J=7)<br>2.42(t, J=7) | M+ = 672 |
| 45 | 3.60(d, J=18)<br>3.44(d, J=18) | 5.03(d, J=5) | 5.54(dd, J=5,8) | 4.63(d, J=13)<br>4.44(d, J=13) | 3.94(s) | 9.31(d, J=8) | 7.46–7.51(m)<br>7.24(dd, J=2,9) | 8.63(br s)<br>8.23(br s) | 8.62(s) overlaps w/pyr H<br>5.20(s)<br>3.30(t, J=7)<br>2.42(t, J=7) | MH+ = 687 |
| 46 | 3.71(d, J=18)<br>3.51(d, J=18) | 5.14(d, J=5) | 5.68(dd, J=5,8) | 4.42(d, J=13)<br>4.32(d, J=13) | 3.90(s) | 9.26(d, J=8) | 7.44–7.47(m)<br>7.21–7.26(m) | 8.61(d, J=7)<br>8.01(d, J=7) | 7.14(d, J=7)<br>5.33(br s)<br>4.78(br s)<br>4.04(br s)<br>3.25(br s) | M+ = 687 |
| 47 | 3.74(d, J=18)<br>3.51(d, J=18) | 5.13(d, J=5) | 5.69(dd, J=5,8) | 4.43(d, J=18)<br>4.35(d, J=18) | 3.99(s) | 9.30(d, J=8) | 7.50(s) | 8.63(d, J=7)<br>8.01(d, J=7) | 8.82(d, J=8)<br>5.32(s)<br>4.28–4.37(m)<br>3.61–3.74(m) | M+ = 688 |
| 48 | 3.40(d, J=18)<br>3.56(d, J=18) | 4.99(d, J=5) | 5.50(dd, J=5,8) | 4.63(d, J=14)<br>4.37(d, J=14) | 3.90(s) | 9.25(d, J=8) | 7.43–7.47(m)<br>7.23(d, J=2)<br>7.20(d, J=2) | 8.61(d, J=7)<br>8.26(d, J=7) | 8.92(d, J=8)<br>5.30(s)<br>4.28–4.37(m)<br>3.60–3.72(m) | M+ = 731 |
| 49 | 3.57(d, J=18)<br>3.41(d, J=18) | 5.00(d, J=5) | 5.51(dd, J=5,8) | 4.61(d, J=13)<br>4.38(d, J=13) | 3.90(s) | 9.28(d, J=8) | 7.43–7.48(m)<br>7.23(d, J=2)<br>7.20(d, J=2) | 8.58(d, J=6)<br>8.26(d, J=7) | 9.13(d, J=7)<br>5.34(s)<br>4.26–4.33(m)<br>2.48–2.53(m)<br>2.01(s)<br>1.85–1.97(m) | M+ = 697 |

Additional R column entry for compound 49: 5.62(br s), 4.25–4.28(m), 2.15(br s), 1.72–1.97(m)

TABLE-continued

NMR DATA

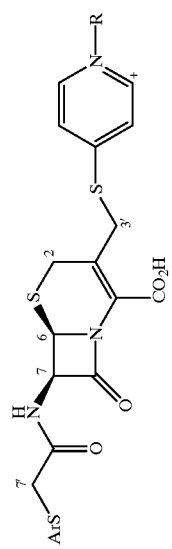

| Cmpd of Ex No | H-2 | H-6 | H-7 | H-3' | H-7' | NH | ArH | S-PyrH | R | MS Data |
|---|---|---|---|---|---|---|---|---|---|---|
| 50 | 3.55(d, J=17)<br>3.39(d, J=17) | 4.99(d, J=5) | 5.49(dd, J=5,8) | 4.66(d, J=13)<br>4.44(d, J=13) | 3.91(d, J=8) | 9.32(s) | 7.38–7.50(m)<br>7.15–7.25<br>(Overlaps<br>with R) | 8.53(d, J=6)<br>8.26(d, J=6) | 9.01(br s)<br>7.15–7.25(m)<br>(Overlaps<br>with ArH)<br>5.28–5.31(m)<br>4.28–4.30(m)<br>3.07–3.10(m)<br>2.84–2.91(m) | $M^+ = 747$ |
| 51 | 3.65(d, J=18)<br>3.44(d, J=16) | 5.05(d, J=5) | 5.62(dd, J=5,8) | 4.52(s) | 4.00(d, J=8) | 9.25(d, J=8) | 7.49–7.40(m)<br>7.25–7.16(m) | 8.42(d, J=7)<br>8.22(d, J=7) | 7.00(d, J=8)<br>6.68(d, J=8)<br>4.70(m)<br>4.24(m)<br>2.21(m) | $MH^- = 763$ |
| 52 | 3.64(d, J=17)<br>3.46(d, J=17) | 5.06(d, J=5) | 5.56(dd, J=5,8) | 4.42–4.58(m)<br>Overlaps<br>with R | 3.93(s) | 9.31(br s) | 7.47–7.51(m)<br>7.26(d, J=8) | 8.53(d, J=6)<br>8.21(d, J=6) | 9.12(br s)<br>7.90(s)<br>7.00(s)<br>5.28(br s)<br>4.42–4.58(m)<br>(Overlaps<br>with H-3')<br>3.90–3.15(m) | $MH^- = 735$ |
| 53 | 3.55(d, J=18)<br>3.40(d, J=18) | 4.99(d, J=5) | 5.50(dd, J=5,8) | 4.58(d, J=14)<br>4.42(d, J=14) | 3.90(s) | 9.37(br s) | 7.43–7.47(m)<br>7.23(d, J=2)<br>7.20(d, J=2) | 8.77(d, J=7)<br>8.21(d, J=7) | 9.26(d, J=8)<br>5.70(d, J=7)<br>3.76(d, J=5)<br>1.77(d, J=7) | $M^+ = 671$ |
| 54 | 3.58(d, J=18)<br>3.42(d, J=18) | 5.01(d, J=5) | 5.47–5.54(m) | 4.37(d, J=14)<br>4.61(d, J=14) | 3.89(s) | 9.24(d, J=8) | 7.43–7.48(m)<br>7.23(d, J=2)<br>7.20(d, J=2) | 8.56(t, J=7)<br>8.24(m) | 5.68<br>(overlaps<br>with H-7)<br>4.17(s)<br>4.04(s)<br>3.07(s)<br>2.85(s) | $M^+ = 671$ |
| 55 | 3.76(d, J=18) | 5.14(d, J=5) | 5.69(dd, J=5,8) | 4.35(d, J=13) | 3.91(s) | 9.29(d, J=8) | 7.40–7.47(m) | 8.66(d, J=7) | 5.24(s) | $MH^- = 634$ |

TABLE-continued

NMR DATA

| Cmpd of Ex No | H-2 | H-6 | H-7 | H-3' | H-7' | NH | ArH | S-PyrH | R | MS Data |
|---|---|---|---|---|---|---|---|---|---|---|
| 56 | 3.55(d, J=18) 3.49(d, J=17) 3.36(d, J=17) | 4.96(d, J=5) | 5.45(dd, J=5,8) | 4.63(d, J=14) 4.26(d, J=14) | 3.84–3.95(m) | 9.22(d, J=8) | 7.22–7.25(m) 7.46–7.48(m) 7.21–7.24(m) | 8.01(d, J=7) 8.63(d, J=7) 8.29(d, J=7) | 4.63(t, J=6) 3.06(t, J=6) | M+ = 650 |
| 57 | 3.73(d, J=18) 3.49(d, J=18) | 5.12(d, J=5) | 5.67(dd, J=5,8) | 4.34(s) | 3.91(s) | 9.29(d, J=8) | 7.46(d, J=2) 7.45(d, J=8) 7.23(dd, J=2,8) | 7.76(s) 2.77(s) | 4.56(t, J=7) 2.99(t, J=7) | (M−H)− = 676 |
| 58 | 3.73(d, J=18) 3.52(d, J=18) | 5.14(d, J=5) | 5.67(dd, J=5,8) | 4.45(d, J=13) 4.36(d, J=13) | 3.92(s) | 9.31(d, J=8) | 7.46(d, J=2) 7.45(d, J=8) 7.23(dd, J=2,8) | 8.69(d, J=7) 7.78–7.83(m) 3.04(q, J=7) 1.28(t, J=7) | 4.64(t, J=6) 2.73(t, J=6) | M+ = 700 |
| 59 | 3.75(d, J=18) 3.52(d, J=18) | 5.16(d, J=5) | 5.69(dd, J=5,8) | 4.39(d, J=12) 4.31(d, J=12) | 3.91(br s) | 9.28(d, J=8) | 7.47(br s) 7.46(d, J=8) 7.23(dd, J=2,8) | 8.63(d, J=7) 7.77(d, J=7) 2.71(s) 2.31(s) | 4.75–4.69(m) 3.03–2.97(m) | MH+ = 678 |
| 60 | 3.52(d, J=18) 3.37(d, J=18) | 4.96(d, J=5) | 5.45(dd, J=5,8) | 4.70(d, J=13) 4.31(d, J=13) | 3.89(s) | 9.20(d, J=8) | 7.43–7.48(m) 7.20–7.24(m) | 8.59(d, J=7) 8.35(d, J=7) | 8.52(t, J=6) 5.19(s) 3.20–3.29(m) 2.56–2.61(t, J=7) | M+ = 707 |
| 61 | 3.66(d, J=18) 3.46(d, J=18) | 4.98(d, J=5) | 5.18(dd, J=5,8) | 4.68(d, J=13) 4.35(d, J=13) | 3.96(s) | 9.22(d, J=8) | 7.50(s) | 8.81(d, J=7) 8.27(d, J=7) | 8.53(t, J=6) 5.18(s) 3.30–3.46(m) 2.55–2.60(t, J=7) | M+ = 707 |
| 62 | 3.72(d, J=18) 3.49(d, J=18) | 5.11(d, J=5) | 5.67(dd, J=5,8) | 4.40(d, J=13) 4.34(d, J=13) | 3.91(s) | 9.27(d, J=8) | 7.46(d, J=2) 7.45(d, J=8) 7.23(dd, J=2,8) | 8.73(d, J=7) 7.97(d, J=7) | 4.61(t, J=6) 3.25(q, J=7) 2.77(t, J=6) 2.45–2.49(m) | (M−H)− = 719 |
| 63 | 3.74(d, J=18) 3.49(d, J=18) | 5.13(d, J=5) | 5.68(dd, J=5,8) | 4.41(d, J=13) 4.34(d, J=13) | 3.99(s) | 9.29(d, J=8) | 7.49(s) | 8.70(d, J=7) 8.00(d, J=7) | 4.64(br s) 4.15(br s) | (M−H)− = 665 |
| 64 | 3.51(d, J=17) | 4.97(d, J=5) | 5.46(dd, J=5,8) | 4.61(d, J=13) | 3.91(s) | 9.23(d, J=8) | 7.45–7.50(m) | 8.70(d, J=7) | 4.51(t, J=7), | MH+ = 683 |

TABLE-continued

NMR DATA

| Cmpd of Ex No | H-2 | H-6 | H-7 | H-3' | H-7' | NH | ArH | S-PyrH | R | MS Data |
|---|---|---|---|---|---|---|---|---|---|---|
| 65 | 3.33(d, J=17) | | | 4.40(d, J=13) | | | 7.22–7.26(m) | 8.27(d, J=7) | 2.92(t, J=7) 2.24–2.20(m) | |
| 66 | 3.52(d, J=17) 3.38(d, J=17) | 4.98(d, J=5) | 5.45(dd, J=5,8) | 4.73–4.85(m) 4.24–4.35(m) | 3.90(s) | 9.22(d, J=8) | 7.46–7.50(m) 7.22–7.26(m) | 8.58–8.67(m) 8.36–8.45(m) | 5.76(s) | $MH^+ = 668$ |
| 67 | 3.50(d, J=17) 3.29(d, J=17) | 4.89(d, J=5) | 5.44(d, J=5) | 4.37(br s) | 3.84(s) | exchanged with $D_2O$ | 7.36–7.44(m) 7.19–7.23(m) | 8.49–8.60(m) 7.92–8.01(m) | 4.56–4.69(m) 2.97–3.08(m) | $MH^+ = 681$ |
| 68 | 3.45(d, J=17) 3.32(d, J=17) | 4.97(d, J=5) | 5.45(dd, J=5,8) | 4.60(d, J=13) 4.44(d, J=13) | 3.92(s) | 9.25(d, J=8) | 7.46–7.50(m) 7.22–7.28(m) | 8.72(d, J=6) 8.29(d, J=6) | 4.33–4.52(m) 2.25–2.37(m) 2.03–2.22(m) | $MH^+ = 695$ |
| 69 | 3.75(d, J=18) 3.51(d, J=18) | 5.14(d, J=5) | 5.71(d, J=5,8) | 4.38(br s) | 3.93(s) | 9.29(d, J=8) | 7.46–7.49(m) 7.25(dd, J=2,9) | 8.65(d, J=7) 7.97(d, J=7) | 5.45(s) | $MH^+ = 643$ |
| 70 | 3.32–3.63(m) | 5.02(d, J=5) | 5.54(dd, J=5,8) | 4.41–4.46(m) | 4.04(s) | 9.23(d, J=8) | 7.45–7.51(m) 7.22–7.25(m) | 8.55(d, J=7) 7.85(d, J=7) | 4.05(m) 3.36(m) 2.88(s) 2.46(m) 2.21(m) | $M-CO_2 = 678$ |
| 71 | 3.71(d, J=18) 3.49(d, J=18) | 5.13(d, J=5) | 5.70(dd, J=5,8) | 4.37(d, J=13) 4.31(d, J=13) | 3.93(s) | 9.32(d, J=8) | 7.45–7.48(m) 7.24(dd, J=2,8) | 8.54(d, J=7) 7.87(d, J=7) | 7.40(d, J=5) 6.71–6.88(m) 5.66(br s) 4.33(d, J=7) | $M^+ = 711$ |
| 72 | 3.49(d, J=18) 3.36(d, J=18) | 4.90(d, J=5) | 5.45(dd, J=5,8) | 4.72(d, J=14) 4.32(d, J=14) | 3.96(d, J=15) 3.89(d, J=15) | 9.34(d, J=8) | 7.49(d, J=2) 7.46(d, J=8) 7.24(dd, J=2,8) | 8.65(d, J=6) 7.99(d, J=6) | 8.60(br s) 4.51(br s) 3.52(br s) 3.01(d, J=15) 2.95(d, J=15) | $MH^+ = 671$ |
| | 3.52(d, J=18) 3.32(d, J=18) | 4.97(d, J=5) | 5.46(dd, J=5,8) | 4.50(d, J=13) 4.40(d, J=13) | 3.91(s) | 9.19(d, J=8) | 7.45–7.50(m) 7.23(dd, J=2,8) | 8.73(d, J=7) 8.29(d, J=7) | 4.60(t, J=6) 3.09(t, J=7) 2.61–2.68(m) 2.72–2.88(m) | $M^+ = 709$ |

We claim:
1. A compound of the formula
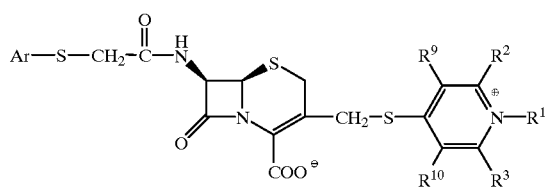
wherein Ar is a group of the formula
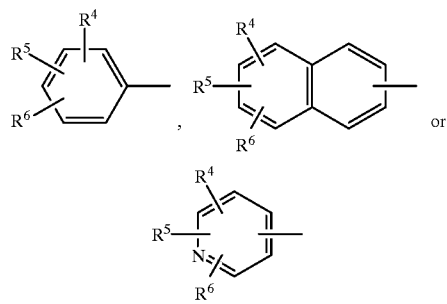
in which $R^4$, $R^5$ and $R^6$ are each independently hydrogen, halogen, trihalomethyl, nitro, amino, hydroxy, hydroxy $(C_1-C_6)$alkyl, $(C_1-C_6)$alkyl, $—(CH_2)_nOR^7$ or $—(CH_2)_nSR^7$; n is an integer of from 1 to 6; $R^7$ is hydrogen or $(C_1-C_6)$alkyl;
$R^1$ is
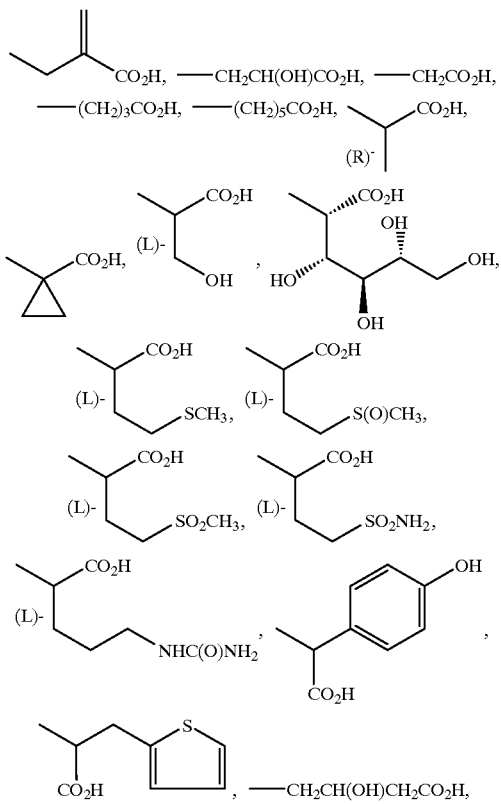
-continued
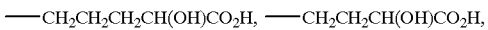
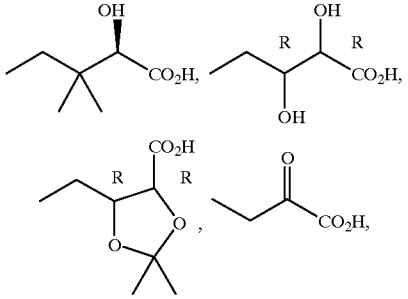
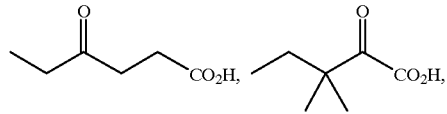
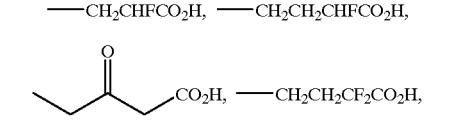
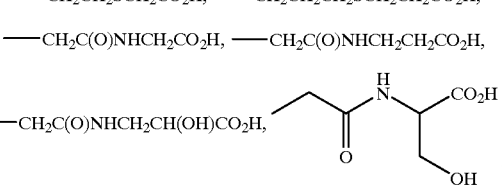
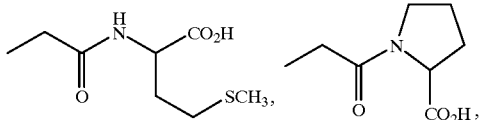
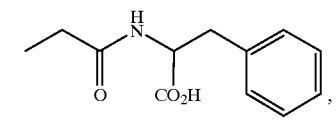
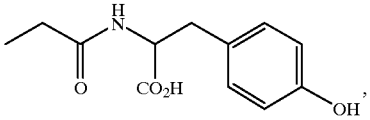
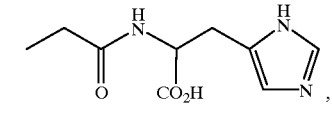
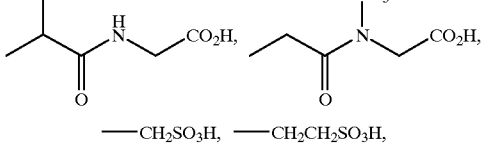
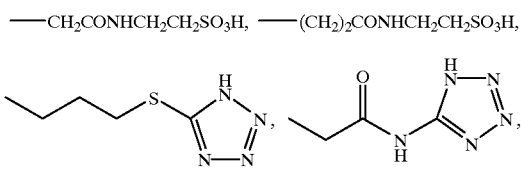

-continued

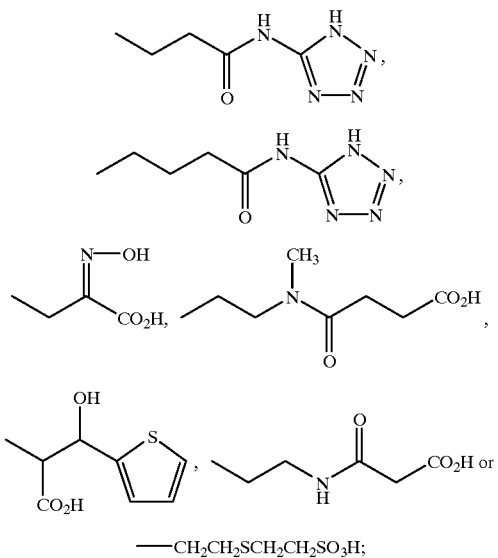

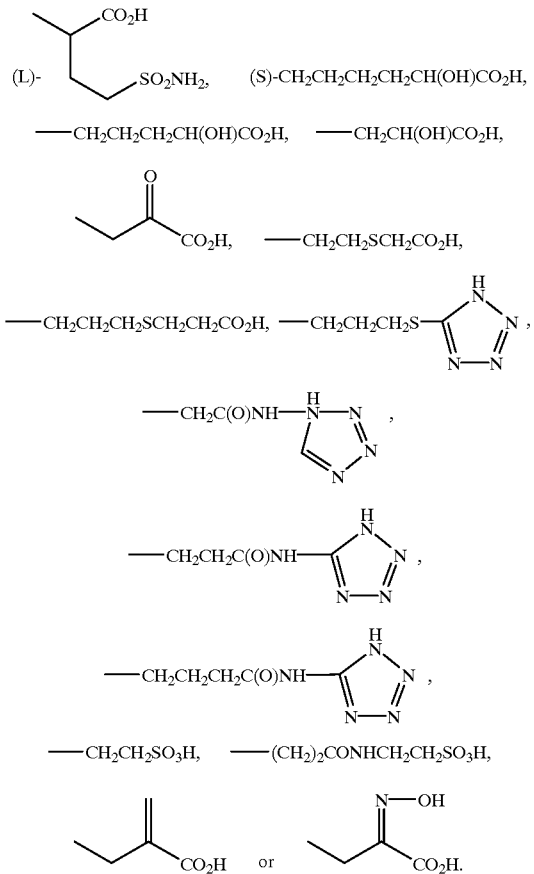

$R^2$, $R^3$, $R^9$ and $R^{10}$ are each independently hydrogen or $(C_1-C_{10})$alkyl; or a pharmaceutically acceptable salt thereof.

2. A compound of claim 1 wherein $R^1$ is

3. A compound of claim 1 wherein Ar is

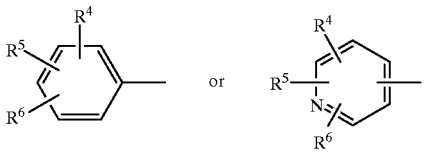

in which $R^4$, $R^5$ and $R^6$ are each independently hydrogen, halogen, $(C_1-C_6)$alkyl, trifluoromethyl, hydroxy, hydroxy $(C_1-C_6)$alkyl or amino.

4. A compound of claim 1 wherein Ar is

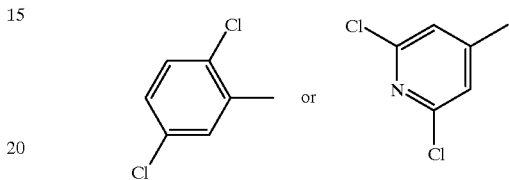

5. A compound selected from the group consisting of:
1-[2-carboxy-2-propen-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[2-carboxy-2-hydroxy ethyl]-4-[[(6R)-trans-2-carboxylate-8-oxo-7-[(2,5-dichlorophenylthio) acetamido]-5-thia-1-azabicyclo[4.2.0]-oct-2-en-3-yl]methylthio]pyridinium inner salt or a pharmaceutically acceptable salt thereof 1-(carboxymethyl)-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[(3-carboxy-1-propyl)]-4-[[(6R)-trans-2-carboxylate-8-oxo-7-[(2,5-dichlorophenylthio)acetamido]-5-thia-1-azabicyclo [4.2.0]-oct-2-en-3-yl]methylthio]pyridinium inner salt or a pharmaceutically acceptable salt thereof 1-[(5-carboxy-1-pentyl)]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[(R)-1-carboxy-1-ethyl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[(1-carboxy-1-cyclopropyl)]-4-[[(6R)-trans-2-carboxylate-8-oxo-7-[(2,5-dichlorophenylthio) acetamido]-5-thia-1-azabicyclo[4.2.0]-oct-2-en-3-yl]methylthio]pyridinium inner salt or a pharmaceutically acceptable salt thereof 1-[(S)-1-carboxy-2-hydroxy-1-ethyl]-4-[[(6R)-trans-2-carboxylate-8-oxo-7-[(2,5-dichlorophenylthio) acetamido]-5-thia-1-azabicyclo[4.2.0]-oct-2-en-3-yl]methylthio]pyridinium inner salt or a pharmaceutically acceptable salt thereof 1-[(1S, 2R, 3S, 4R)-1-carboxy-2,3,4,5-tetrahydroxy pent-1-yl]-4-[[(6R)-trans-2-carboxylate-8-oxo-7-[(2,5-dichlorophenylthio)acetamido]-5-thia-1-azabicyclo [4.2.0]-oct-2-en-3-yl]methylthio]pyridinium inner salt or a pharmaceutically acceptable salt thereof 1-[(S)-1-carboxy-3-(thiomethyl)prop-1-yl]-4-[[(6R)-trans-2-carboxylate-8-oxo-7-[(2,5-dichlorophenylthio) acetamido]-5-thia-1-azabicyclo[4.2.0]-oct-2-en-3-yl]methylthio]pyridinium inner salt or a pharmaceutically acceptable salt thereof 1-[(S)-1-carboxy-3-(methylsulfinyl)prop-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[(S)-1-carboxy-3-(methylsulfonyl)prop-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[(S)-3-aminosulfonyl-1-carboxyprop-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[(S)-4-(aminocarbonyl)amino-1-carboxybut-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[(S)-1-carboxy-(4-hydroxy phenyl)methyl]-4-[[(6R)-trans-2-carboxylate-8-oxo-7-[(2,5-dichlorophenylthio)acetamido]-5-thia-1-azabicyclo [4.2.0]-oct-2-en-3-yl]methylthio]pyridinium inner salt or a pharmaceutically acceptable salt thereof 1-[(S)-1-carboxy-2-(2-thienyl)ethyl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[3-carboxy-2-hydroxy-1-propyl]-4-[[(6R)-trans-2-carboxylate-8-oxo-7-[(2,5-dichlorophenylthio)acetamido]-5-thia-1-azabicyclo [4.2.0]-oct-2-en-3-yl]methylthio]pyridinium inner salt or a pharmaceutically acceptable salt thereof 1-[(S)-5-carboxy-5-hydroxypent-1-yl]-4-[(6R)-trans-2-carboxylate-8-oxo-7-[(2 5-dichlorophenylthio)acetamido]-5-thia-1-azabicyclo[4.2.0]-oct-2-en-3-yl]methylthio]pyridinium inner salt or a pharmaceutically acceptable salt thereof 1-[(S)-5-carboxy-5-hydroxypent-1-yl]-4-[[(6R)-trans-2-carboxylate-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof 1-[(S)-4-carboxy-4-hydroxybut-1-yi]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[(S)-4-carboxy-4-hydroxybut-1-yl]-4-[[(6R)-trans-2-carboxylate-8-oxo-7-[(2.6-dichloropyridin-4-yl)thioacetamido]-5-thia-1-azabicyclo[4.2.0]-oct-2-en-3-yl]methylthio]pyridinium inner salt or a pharmaceutically acceptable salt thereof 1-[(R)-4-carboxy-4-hydroxybut-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[(R)-4-carboxy-4-hydroxybut-1-yl]-4-[[(6R)-trans-2-carboxylate-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof 1-[(S)-3-carboxy-3-hydroxyprop-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[(S)-3-carboxy-3-hydroxyprop-1-yl]-4-[[(6R)-trans-2-carboxylate-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof 1-[2-carboxy-2-hydroxy ethyl]-4-[[(6R)-trans-2-carboxylate-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof 1-[(S)-3-carboxy-3-hydroxy-2,2-dimethylprop-1-yl]-4-[(6R)-trans-2-carboxylate-8-oxo-7-[(2,5-dichlorophenylthio)acetamido]-5-thia-1-azabicyclo 4.2.0]-oct-2-en-3-yl]methylthio]pyridinium inner salt or a pharmaceutically acceptable salt thereof 1-[(2R,3R)-3-carboxy-2,3-dihydroxyprop-1-yl]-4-[[(6R)-trans-2-carboxylate-8-oxo-7-[[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[(2,2-dimethyl-4-carboxydioxolan-5-yl)methyl)4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[2-carboxy-2-oxoeth-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[2-carboxy-2-oxoeth-1-yl]-4-[[(6R)-trans-2-carboxylate-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof 1-[3-carbomethoxy-2-oxoprop-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[4-carboxy-2-oxoprop-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[2,2-dimethyl-3-carboxy-3-oxoprop-1-yl]-4-[[(6R)-trans-2-carboxylate-8-oxo-7-1(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[2-carboxy-2-fluoroeth-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[3-carboxy-3-fluoroprop-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[3-carboxy-3,3-difluoroprop-1-yl]-4-[[(6R)-trans-2-carboxylate-8-oxo-7-[(2,5-dichlorophenylthio)acetainido]-5-thia-1-azabicyclo[4.2.0]-oct-2-en-3-yl]methylthio]pyridinium inner salt or a pharmaceutically acceptable salt thereof 1-[2-(carboxymethylthio)eth-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[3-(2-carboxyethylthio)-1-propyl]-4-[[(6R)-trans-2-carboxylate-8-oxo-7-1(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[N-(carboxymethyl)-aminocarbonylmethyl]-4-[[(6R)-trans-2-carboxylate-8-oxo-7-[(2,5-dichlorophenylthio)acetamido]-5-thia-1-azabicyclo [4.2.0]-oct-2-en-3-yl]methylthio]pyridinium inner salt or a pharmaceutically acceptable salt thereof 1-[N-(carboxymethyl)-aminocarbonylmethyl]-4-[[(6R)-trans-2-carboxylate-8-oxo-7-[(2,4,5-trichlorophenylthio)acetamido]-5-thia-1-azabicyclo[4.2.0]-oct-2-en-3-yl]methylthio]pyridinium inner salt or a pharmaceutically acceptable salt thereof 1-[N-(carboxymethyl)-aminocarbonylmethyl]-4-[[(6R)-trans-2-carboxylate-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof 1-[N-(2-carboxyethyl)-aminocarbonylmethyl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[N-(2-carboxyethyl)-aminocarbonylmethyl]-4-[[(6R)-trans-2-carboxylate-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof 1-[N-(2-carboxyethyl-2-hydroxy)aminocarbonylmethyl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[N-(1-carboxy-2-hydroxyeth-1-yl)aminocarbonylmethyl]-4-[[(6R)-trans-2-carboxylate-8-oxo-7-[(2,5-dichlorophenylthio)acetamido]-5-thia-1-azabicyclo [4.2.0]-oct-2-en-3-yl]methylthio]pyridinium inner salt or a pharmaceutically acceptable salt thereof 1-[N-(1-carboxy-2-hydroxyeth-1-yl)aminocarbonylmethyl]-4-[[(6R)-trans-2-carboxylate-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof 1-[N-(1-carboxy-3-thiomethylprop-1-yl)aminocarbonylmethyl]-4-[[(6R)-trans-2-carboxylate-8-oxo-7-[(2,5-dichlorophenylthio)acetamido]-5-thia-1-azabicyclo [4.2.0]-oct-2-en-3-yl]methylthio]pyridinium inner salt or a pharmaceutically acceptable salt thereof 1-[2-((S)-N-prolyl)-2-oxoeth-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[N-(1-carboxy-2-phenylethyl)aminocarbonylmethyl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[N-(1-carboxy-2-(4-hydroxyphenyl)ethyl)aminocarbonylmethyl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[N-(1-carboxy-2-histidylethyl )aminocarbonylmethyl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[N-(carboxymethyl)-1-aminocarbonyleth-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[N-methyl-N-(carboxymethyl)aminocarbonylmethyl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-(sulfomethyl)-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-(2-sulfoeth-1-yl)-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 2,6-dimethyl-1-(2-sulfoeth-1-yl)-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 2-ethyl-1-(2-sulfoethyl)-4-[[(6R)-trans-2-carboxylate-8-oxo-7-[(2,5-dichlorophenylthio)acetamido 1-5-thia-1-azabicyclo[4.2.0]-oct-2-en-3-yl]methylthio]pyridinium inner salt or a pharmaceutically acceptable salt thereof 2,3-dimethyl-1-(2-sulfoethyl)-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[N-(2-sulfoethyl)aminocarbonylmethyl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[N-(2-sulfoethyl)aminocarbonylmethyl]-4-[[(6R)-trans-2-carboxylate-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof 1-[N-(2-sulfoethyl)-2-aminocarbonylethyl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-6N-(2-sulfoethyl)-2-aminocarbonylethyl]-4-[[(6R)-trans-2-carboxylate-8-oxo-7-[(2,6-dichloropyridin-4-yl)thioacetamido]-5-thia-1-azabicyclo[4.2.0]-oct-2-en-3-yl]methylthio]pyridinium inner salt or a pharmaceutically acceptable salt thereof 1-[3-(5-tetrazolylthio)prop-1-yl]-4-[[(6)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[N-(5-tetrazolyl)aminocarbonylmethyl]-4-[[(6R)-trans-2-carboxylate-8-oxo-7-[(2,5-dichlorophenylthio)acetamido]-5-thia-1-azabicyclo[4.2.0]-oct-2-en-3-yl]

methylthio]pyridinium inner salt or a pharmaceutically acceptable salt thereof

1-[N-(5-tetrazolyl)-2-aminocarbonyleth-1-yl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 1-[N-(5-tetrazolyl)-3-aminocarbonylprop-1-yl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 1-[2-carboxy-2-(hydroxyimino)eth-1-yl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 1-[N-methyl-N-(3-carboxy-1-oxoprop-1-yl)-2-aminoeth-1-yl]-4-[[(6R)-trans-2-carboxylate-8-oxo-7-[(2,5-dichlorophenylthio)acetamido]-5-thia-1-azabicyclo [4.2.0]-oct-2-en-3-yl]methylthio]pyridinium inner salt or a pharmaceutically acceptable salt thereof 1-[1-carboxy-2-hydroxy-2-(2-thienyl)eth-1-yl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 1-[N-(2-carboxy-1-oxoeth-1-yl)-2-aminoeth-1-yl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof; and 1-[2-(2-sulfoethylthio)eth-1-yl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof.

6. A compound selected from the group consisting of

1-[2-carboxy-2-propen-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[2-carboxy-2-hydroxy ethyl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 1-[(S)-3-aminosulfonyl-1-carboxyprop-1-yl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 1-[(S)-5-carboxy-5-hydroxypent-1-yl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 1-[(S)-4-carboxy-4-hydroxybut-1-yl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 1-[(R)-4-carboxy-4-hydroxybut-1-yl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 1-[(S)-3-carboxy-3-hydroxyprop-1-yl]-4-[[(6R)-trans-2-carboxylate-8-oxo-7-[(2,6-dichloropyridin-4-yl)thioacetamido]-5-thia-1-azabicyclo[4.2.0]-oct-2-en-3-yl] methylthio]pyridinium inner salt or a pharmaceutically acceptable salt thereof 1-[2-carboxy-2-oxoeth-1-yl]-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[2-carboxy-2-oxoeth-1-yl]-4-[[(6R)-trans-2-carboxylate-8-oxo-7-[(2,6-dichloropyridin-4-yl)thioacetamido]-5-thia-1-azabicyclo[4.2.0]-oct-2-en-3-yl]methylthio] pyridinium inner salt or a pharmaceutically acceptable salt thereof 1-[2-(carboxymethylthio)eth-1-yl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 1-[3-(2-carboxyethylthio)-1-propyl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 1-[N-(2-carboxyethyl)-aminocarbonylmethyl]-4-[[(6R)-trans-2-carboxylate-8-oxo-7-[(2,6-dichloropyridin-4-yl)thioacetamido]-5-thia-1-azabicyclo[4.2.0]-oct-2-en-3-yl] methylthio]pyridinium inner salt or a pharmaceutically acceptable salt thereof 1-(2-sulfoeth-1-yl)-4-[[(6R)-trans-2-carboxylate-8-oxo-7-[(2,5-dichlorophenylthio)acetamido]-5-thia-1-azabicyclo [4.2.0]-oct-2-en-3-yl]methylthio]pyridinium inner salt or a pharmaceutically acceptable salt thereof 2,6-dimethyl-1-(2-sulfoeth-1-yl)-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 2,3-dimethyl-1-(2-sulfoethyl)-4-[[(6R)-trans-2-carboxylate-8-oxo-7-[(2,5-dichlorophenylthio)acetamido]-5-thia-1-azabicyclo[4.2.0]-oct-2-en-3-yl]methylthio]pyridinium inner salt or a pharmaceutically acceptable salt thereof 1-[N-(2-sulfoethyl)-2-aminocarbonylethyl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 1[-N-(2-sulfoethyl)-2-aminocarbonylethyl]-4-[[(6R)-trans-2-carboxylate-8-oxo-7-[(2,6-dichloropyridin-4-yl)thioacetamido]-5-thia-1-azabicyclo[4.2.0]-oct-2-en-3-yl] methylthio]pyridinium inner salt or a pharmaceutically acceptable salt thereof 1-[3-(5-tetrazolylthio)prop-1-yl]-4-[[(6R)-trans-2-carboxylate-8-oxo-7-[(2,5-dichlorophenylthio)acetamido]-5-thia-1-azabicyclo [4.2.0]-oct-2-en-3-yl] methylthio]pyridinium inner salt or a pharmaceutically acceptable salt thereof 1-[N-(5-tetrazolyl)aminocarbonylmethyl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 1-[N-(5-tetrazolyl)-2-aminocarbonyleth-1-yl]-4-[[(6R)-trans-2-carboxylate-8-oxo-7-[(2,5-dichlorophenylthio)acetamido]-5-thia-1-azabicyclo[4.2.0]-oct-2-en-3-yl] methylthio]pyridinium inner salt or a pharmaceutically acceptable salt thereof 1-[N-(5-tetrazolyl)-3-aminocarbonylprop-1-yl]-4-[[(6R)-trans-2-carboxylate-8-oxo-7-[(2,5-dichlorophenylthio)acetamido]-5-thia-1-azabicyclo [4.2.0]-oct-2-en-3-yl]methylthio]pyridinium inner salt or a pharmaceutically acceptable salt thereof, and 1-[2-carboxy-2-(hydroxyimino)eth-1-yl]-4-[[(6R)-trans-2-carboxylate-8-oxo-7-[(2,5-dichlorophenylthio)acetamido]-5-thia-1-azabicyclo [4.2.0]-oct-2-en-3-yl]methylthio]pyridinium inner salt or a pharmaceutically acceptable salt thereof.

7. A pharmaceutical composition comprising an effective antibacterial amount of a compound of claim 1 and a pharmaceutically acceptable carrier or excipient.

8. A method of treating a bacterial infection which comprises administering to a host afflicted with such infection an effective antibacterial amount of a compound of claim 1.

9. A method of treating a bacterial infection caused by a strain of methicillin-resistant *Staphylococcus aureus* which comprises administering to a host afflicted with such infection an effective antibacterial amount of a compound of claim 1.

* * * * *